(12) United States Patent
Prystupa et al.

(10) Patent No.: US 10,585,044 B2
(45) Date of Patent: Mar. 10, 2020

(54) HIGH EFFICIENCY MULTIPLEXING

(71) Applicant: 10103560 Canada Ltd., Winnipeg (CA)

(72) Inventors: David Prystupa, Pinawa (CA); John Pacak, Winnipeg (CA)

(73) Assignee: 10103560 Canada Ltd., Winnipeg, MB (CA)

( * ) Notice: Subject to any disclaimer, the term of this patent is extended or adjusted under 35 U.S.C. 154(b) by 0 days.

(21) Appl. No.: 15/987,279

(22) Filed: May 23, 2018

(65) Prior Publication Data

US 2018/0340893 A1    Nov. 29, 2018

Related U.S. Application Data

(60) Provisional application No. 62/510,825, filed on May 25, 2017.

(51) Int. Cl.
| | | |
|---|---|---|
| *G01N 21/86* | (2006.01) | |
| *G01J 3/28* | (2006.01) | |
| *G01N 21/64* | (2006.01) | |
| *G01N 21/35* | (2014.01) | |
| *G01N 27/62* | (2006.01) | |
| *G01J 3/00* | (2006.01) | |
| *G01N 21/85* | (2006.01) | |
| *G01N 27/447* | (2006.01) | |
| *H01J 49/40* | (2006.01) | |
| *G01N 21/65* | (2006.01) | |
| *G01N 21/552* | (2014.01) | |

(52) U.S. Cl.
CPC ............ *G01N 21/86* (2013.01); *G01J 3/28* (2013.01); *G01J 3/00* (2013.01); *G01N 21/552* (2013.01); *G01N 21/6408* (2013.01); *G01N 21/65* (2013.01); *G01N 21/85* (2013.01); *G01N 27/44721* (2013.01); *G01N 27/622* (2013.01); *G01N 2021/3595* (2013.01); *G01N 2201/0675* (2013.01); *H01J 49/40* (2013.01)

(58) Field of Classification Search
CPC . G01J 3/00; G01N 2021/3595; G01N 21/552; G01N 21/6408; G01N 21/65; G01N 21/85; G01N 21/86; G01N 2201/0675; G01N 27/44721; G01N 27/622; H01J 49/40
USPC ................................. 356/432–448, 213–236
See application file for complete search history.

(56) References Cited

U.S. PATENT DOCUMENTS

2008/0137512 A1* 6/2008 Chol .................. G11B 7/083
                                                               369/103

* cited by examiner

*Primary Examiner* — Tri T Ton
(74) *Attorney, Agent, or Firm* — Adrian D. Battison; Ade & Company Inc.; Michael R. Williams

(57) ABSTRACT

In a method for measuring radiation, the radiation is temporally and/or spatially separated by a modulator to direct at least N different combinations of radiation incident on each region into at least two and fewer than N distinct directions. The total intensity of radiation in each direction is measured with a detector for each modulator configuration and the detector outputs are analyzed statistically to obtain information relating to the spectral properties of the radiation. In this way substantially all of the energy received at the entrance aperture of a measurement device is encoded into multiple outputs and the multiplexed output is received by a small number of detectors.

33 Claims, 20 Drawing Sheets

HIGH EFFICIENCY MULTIPLEXING

This application claims the benefit under 37USC 113 (e) of Provisional Application 62/510,825 filed May 25, 2017, the disclosure of which is incorporated herein by reference.

This invention relates to the measurement of wave fields or particle fluxes using spatial and/or temporal modulation. The wave fields may include spatial variation in at least one characteristic or dependent variable. The invention applies to electromagnetic waves, matter waves and pressure (sound) waves. The waves may be transverse or longitudinal. The spatial variation or dependent variable in electromagnetic waves may be amplitude, intensity, frequency, wavelength, phase, polarization direction of propagation or location of origin.

Electromagnetic waves may also be described as a flux of photons. Matter waves may also be described as particle fluxes of electrons, neutrons, atoms, ions, molecules, or assemblies of these. The spatial variation in particle fluxes may relate to any property of the matter including location of origin, velocity, acceleration, charge, mass, spin, quantum state, magnetic or electric dipole. The spatial variation in acoustic waves may be amplitude, intensity, velocity, phase, or location of origin.

The method of measurement can be used in many different fields including but not limited to crystallography, spectroscopy, interferometry, spectral imaging, imaging, positron emission tomography, microscopy, electron microscopy, mass spectroscopy, ion mobility spectroscopy and capillary electrophoresis. The arrangement herein can also be used in communications systems, radar systems or other uses as specifically set out above.

One example is disclosed in U.S. Pat. No. 8,345,254 (Prystupa) issued Jan. 1, 2013 for analyzing optically thin heterogeneous samples, the disclosure of which can be studied further information or the disclosure of which is incorporated herein by reference.

Another example is disclosed in PCT published application 2016/0011548 (Prystupa) published 28 Jan. 2016 for analyzing light and ultrasound reflected by a moving sample, the disclosure of which can be studied for further information or the disclosure of which is incorporated herein by reference.

Another example is disclosed in PCT published application 2018/018155 published 1 Feb. 2018 for separating particles, the disclosure of which can be studied for further information or the disclosure of which is incorporated herein by reference. Also the main features of this disclosure are included for completeness hereinafter.

BACKGROUND OF THE INVENTION

The invention is an extension of concepts developed primarily in the field of multiplex spectroscopy. The field of spectroscopy has an extensive body of literature. The description is intended only as a summary with more detail given only for points salient to the present invention. The reader is referred to Wolfgang Demtroder, Laser Spectroscopy: Basic Concepts and Instrumentation, 2nd Edition. Springer Verlag, New York (1982) for a practical description of the topic or Max Born and Emil Wolf, Principles of Optics, 7th Edition, Cambridge University Press (2002) for a rigorous discussion of the topic.

Hadamard spectrometers, which combine features of a dispersive instrument with multiplexing are well described by Martin Harwit (1979). The general design of a Hadamard spectrometer includes an entrance slit, a collimating element, a diffractive element, a spatial mask, and a detector, along with focusing optics and folding mirrors at various points along the optical path. In some designs, the order of the diffracting element and spatial filter are interchanged. Electromagnetic radiation is dispersed into wavebands by the diffractive element and focused onto a spatial filter, which directs some, but not all of the wavebands to a detector. The detector measures the intensity of electromagnetic radiation for a series of different spatial filters and a series of equations is solved to deduce the intensity of each waveband in accordance with a weighting scheme. For a fuller discussion of the topic see Neil J. A. Sloane and Martin Harwit. Masks for Hadamard transform optics, and weighing designs APPLIED OPTICS 15(1) 107-114 (1976).

Early Hadamard instruments, for example that shown in U.S. Pat. No. 3,578,980 (Decker) issued May 18, 1971 generated a series of Hadamard spatial masks by stepwise movement of a master mask. These systems faced problems with mask alignment leading to several technical advances, none of which were wholly satisfactory. A variant on this design was devised by U.S. Pat. No. 3,586,442 (Tripp) issued Jun. 22, 1971 whereby spatially encoded wavebands are incident on the dispersive element a second time so as to undo the dispersion and concentrate the radiation field on a detector. Hadamard systems based on rotating masks were developed. U.S. Pat. No. 6,271,917 (Hagler) issued Aug. 7, 2001 noted the step in transmission of a binary mask produces ringing under Fourier analysis and proposed mask slits with graded transmission.

Hadamard methods have been applied to interferometers to produce a hybrid Fourier Transform spectrometer. In U.S. Pat. No. 4,750,834 issued Jun. 14, 1988 Fateley et al. describe a method placing an electrically alterable mask in the plane of an interference pattern. Fateley et al. also provide a method for reducing the interferogram centreburst for FTIR spectrometers in U.S. Pat. No. 5,488,474 issued Jan. 30, 1996. The present invention extends these methods to provide improved signal-to-noise.

In U.S. Pat. No. 4,856,897 issued Aug. 15, 1989 Fateley et al. describe a Raman spectrometer based on a Hadamard electro-optical mask and a single detector. The present invention has an objective to improve the signal-to-noise performance of this design.

More recently, Hadamard designs based on masks generated dynamically by the electro-optic effect (liquid crystals) such as in U.S. Pat. No. 5,235,461 (Kirsch) issued Aug. 10, 1993 or electromechanical effect (micromirror arrays) such as in U.S. Pat. No. 5,504,575 issued Apr. 2, 1996 have been proposed. These approaches suffer from several problems. The duty cycle and consequently sampling rate is limited by the transition time for the mask to transition from one defined state to another defined state. In liquid crystal based designs, the contrast between transmissive and absorbing mask regions is less than 10 bits limiting the precision attainable by the instrument. The duty cycle of micromirror based designs is limited by thermal loading. Furthermore, micromirror designs suffer from diffraction and a non-unity packing fraction. Another recent Hadamard variant illuminates a fixed array of Hadamard masks and measures the transmitted pattern with a focal plane array such as in U.S. Pat. No. 5,050,989 (Van Tassel) issued Sep. 24, 1991. This design has the advantage of being mechanically robust with no moving parts, but has the disadvantage of requiring a large focal plane array. In practical terms, this approach is limited to the visible region of the spectrum where silicon based focal plane arrays are inexpensive.

Spatial dimensions can be multiplexed in the same way as spectral dimensions. The general case is spectral imaging, which produces a data cube with spatial and spectral dimensions. Coifman el al describe an apparatus for multi spectral imaging using a mosaic array of filters in U.S. Pat. No. 758,972 issued Sep. 15, 2009. In U.S. Pat. No. 8,345,254 multiplexing is extended even further to amplify otherwise weak signals. The volume of information in a data cube and the requisite processing requirements led to the development of compressive sampling schemes based on the idea that correlation between points in the cube can be used to reduce the number of parameters required to describe the cube. A fuller description is given by McMackin et al in U.S. Pat. No. 8,717,484 issued May 6, 2014.

A key drawback common to all of the Hadamard variants noted above is that even if optical losses are neglected, only half of the EM radiation entering the entrance aperture is received by the detector(s), on average. This limitation is partially overcome by the arrangement shown in U.S. Pat. Nos. 4,615,619 and 4,799,795 (Fateley) issued Oct. 7, 1986 and Jan. 24, 1989, respectively, who proposed using an array of electro-optical filters that can both transmit and reflect EM radiation to generate standard Hadamard masks. Fateley notes in connection with FIG. 5 that both transmitted and reflected radiation can be measured which could in principle improve the effective throughput. However, the implementation given by Fateley provides a modulation of only 50% (from 5% transmission to 55% transmission). Effectively only half of the EM radiation entering the entrance aperture is used. Fateley does not provide any disclosure about how to use the information from a second detector. A further limitation of all the Hadamard variants noted above is that the best spectral resolution achievable is limited by the fixed geometry of the mask element size.

A Hadamard Transform Time-of-Flight Mass Spectrometer was first described by Brock et al (1998). Ions are continuously introduced via an electrospray needle, skimmed, accelerated and collimated. A collimated ion beam is incident on a Bradbury-Nielsen shutter, which either passes the ion beam undeflected toward the detector or deflects the ion beam above and below the beam axis. The apparatus was later modified (Trapp, 2004) by the addition of detectors above and below the beam axis so that both the direct and deflected beams are measured. The modification increased the duty cycle close to 100% and improved the SNR by 29% compared with the earlier version. An improvement of 44% was expected on theoretical grounds. The difference is attributed to imperfect separation of the ion flux contributing to the wrong detector channel. In both versions, the shutter is temporally modulated according to the rows of a Hadamard matrix to pass packets of ions with pseudo random time shifts. Each packet spreads out in the field free zone with the lightest ions traveling the fastest. The detector receives the superposition of time shifted packets as a time sequence for each row. The inverse Hadamard transform is performed to recover the original mass distribution within each packet. In subsequent work Hudgens et al modulated the ion source to produce Hadamard patterns.

Brock, A.; Rodriguez, N.; Zare, N. Hadamard Transform Time-of-Flight Mass Spectroscopy. Anal. Chem., 70, 3735-3741 (1998).

Trapp, O.; Kimmel, J. R.; Yoon, O. K.; Zuleta, I. A.; Fernandez, F. M.; Zare, R. N. Continuous Two Channel Time-of-Flight Mass Spectroscopic Detection of Electrosprayed Ions. Agnew. Chem. Int. Ed. 43, 6541-6544 (2004).

Hudgens, J. W.; Bergeron, D. A Hadamard transform electron ionization time-of-flight mass spectrometer. REVIEW OF SCIENTIFIC INSTRUMENTS 79(1): 014102 (2008).

The disclosures of each of the above references is incorporated herein by reference or can be studied for further details of constructions which can be used herein.

SUMMARY OF THE INVENTION

The invention is a modulation system and method of analysis for waves and particle fluxes. Those skilled in physics will understand that the physical phenomena measured by the invention have both particle and wave descriptions and the choice of description is a matter of convenience. The modulation may be spatial, temporal, or both. The waves may by electromagnetic waves, matter waves or pressure waves.

According to one definition of the invention there is provided a method for measuring one or more properties of an incident radiation comprising the steps of:
  collecting the incident radiation to be measured;
  dividing the incident radiation into N packets, each packet containing radiation with a different value of a first property;
  separating said radiation packets temporally or spatially using a temporal or spatial modulator and varying the modulator using a modulation sequence to direct N different combinations of incident radiation packets into at least two distinct paths where the sum of radiation intensity for all distinct paths is at least 60% of the total incident radiation;
  measuring the total intensity of radiation in each path with a detector for each modulator configuration to provide a plurality of detector outputs;
  analyzing the detector outputs statistically to obtain information relating to the properties of the radiation to be measured;
  wherein the modulator configuration sequence includes at least two configurations for which each packet is directed into said distinct paths.

In one embodiment the radiation is spatially separated by source location, energy, frequency, wavelength, phase or polarization and directed into N>2 different regions to be characterized into a measurement surface and wherein the modulator is a spatial modulator placed at said measurement surface.

In another embodiment the radiation is temporally separated using a gate modulator.

According to another definition of the invention there is provided a method for measuring one or more properties of an incident radiation comprising the steps of:
  collecting the incident radiation to be measured;
  directing the incident radiation to a temporal modulator or a spatial modulator or a temporal and spatial modulator;
  said modulator cycling through a sequence of M configurations, in each configuration dividing incident radiation into N portions according to the position and/or time the radiation is incident on the modulator, and directing a majority of each portion of incident radiation into one of P distinct paths where the sum of radiation intensity for all portions and all paths is at least 60% of the incident radiation intensity;
  measuring the total intensity of radiation in each path with a detector for each modulator configuration to provide a plurality of detector outputs; analyzing the detector outputs statistically to obtain information relating to the properties of the radiation to be measured;

wherein P is greater than or equal to two and less than N; and wherein M is greater than or equal to N and the modulator configuration sequence includes at least two configurations for which a majority of each portion is directed into different paths.

In one embodiment the radiation is spatially divided into N>2 portions by source location, energy, frequency, wavelength, phase or polarization and directed into N different regions to be characterized into a measurement surface and wherein the modulator is a spatial modulator placed at said measurement surface.

In another embodiment the radiation is temporally divided into N>2 portions using, for example, a gate modulator which is modulated according to said sequence.

Preferably the sequence of configurations of the modulator are chosen such that a matrix representation of the sequence of configurations Z has the property that $Z^T Z$ is non-singular; wherein Z has MP rows and N columns, and wherein each row of Z represents the measurement at one detector and each column of Z represents one range for a particle flux parameter. The elements of Z represent the fraction of particle flux from each range received by the detector specified by the row for one measurement.

According to another definition of the invention there is provided a method for measuring one or more dependent variables of an incident radiation within intervals of an independent variable comprising the steps of:

collecting the incident radiation to be measured;

directing more than half of incident radiation in each interval into one of at least two distinct paths with a spatial modulator or a temporal modulator, said modulator undergoing a sequence of configurations such that each member of the sequence directs a different combination of incident radiation within intervals into each path where the sum of radiation intensity for all distinct paths is at least 60% of the total incident radiation;

measuring the total intensity of radiation in each path with a detector for each modulator configuration to provide a plurality of detector outputs;

analyzing the detector outputs statistically to obtain information relating to the dependent variables of the radiation to be measured.

The term "gate" or "gate modulator" used herein refer to a device that performs the function of taking a flux or particles and delivering more than half of that flux of particles to at least two different destinations at different times. One example of a gate is a multiplexer.

The terms "division" and "range" are used interchangeably. Both refer to intervals of the independent parameter, generally space or time, but also parameters that are correlated with space and time parameters.

The terms "statistically" and "statistical analysis" refer to analysis methods based on multivariate statistics, correlation and probability whether calculated directly as in at least squares or indirectly as in neural networks.

This is a general description with no reference to the number of modulator configurations, type of modulator, or type of variable. This definition includes both partially and fully determined systems of equations. Dependent means a property of the radiation and independent can be a property of the radiation or something unrelated like time or space.

In one embodiment the radiation is spatially separated by an independent property chosen from the set of source location, energy, frequency, wavelength, phase or polarization and directed into N>2 different regions to be characterized into a measurement surface and wherein the modulator is a spatial modulator placed at said measurement surface.

In another embodiment the independent property is time and radiation received over a period T is temporally separated using a gate modulator into N>2 time slices. The time slices can be of equal length T/N, or of unequal length. Time slices of equal length may be useful for measuring the shape of a laser pulse where the dependent property is intensity. The gate modulator in a time of flight optical spectrometer may divide a pulse of photons traveling through a dispersive medium into unequal time slices to measure the photon flux in equal wavelength intervals.

Preferably the number of different configurations of the modulator is greater than or equal to the number of divisions of the independent property. This provides a guarantee that all variables can be solved.

Preferably the modulator configuration sequence includes at least two configurations for each division in which a majority of radiation within that division is directed into different paths.

Preferably each path has a plurality of detectors wherein each detector measures radiation traveling along the path within a different energy range.

In one embodiment the radiation to be measured is from a dispersive spectrometer.

In one embodiment the radiation to be measured is from a Fourier Transform spectrometer.

In one embodiment the radiation to be measured is from an imaging spectrometer. In this embodiment, each path may have a plurality of detectors wherein each detector measures radiation emanating from a different set of regions in the object to be observed.

In one embodiment the radiation to be measured is from an interference pattern.

In one embodiment the radiation to be measured is from a diffractometer.

In one embodiment the radiation to be measured is Raman scattered.

In one embodiment the radiation to be measured is from a grain kernel.

In one embodiment the spatial modulator is refractive.

In one embodiment the spatial modulator is reflective.

In one embodiment the spatial modulator is diffractive.

In one embodiment the detector on each path produces an analog voltage and that analog voltage has a base voltage level subtracted prior to conversion to digital form.

In one embodiment, the invention receives waves with at least one property varying with position and time, encodes the property spatially along two or more paths with a spatial modulator, encodes the property temporally along each path with a temporal modulator measures the wave intensity temporally on each path with a detector, and analyzes the information from all of the detectors to provide information about the waves incident on the analyzer.

That is typically, a sequence of measurements is made with the spatial modulator encoding the wave property that varies with position differently for each measurement in the sequence. The sequence may be repeated to further improve the signal-to-noise ratio. In this embodiment, the invention is conceptually intermediate between a single detector multiplexing instrument such as a Fourier or Hadamard spectrometer and a non-multiplexed linear array of detectors. The invention provides a signal-to-noise ratio superior to conventional multiplexing and close to a linear array of detectors, while using a fraction of the number of detectors.

That is, in another embodiment, the invention receives waves with at least one property varying with time, receives the waves at a detector that produces an analogue signal proportional to a wave property, modulates the analogue signal temporally into two or more integrating devices, and analyzes the information from all of the integrating devices to provide information about the waves incident on the analyzer.

This embodiment provides a method to measure the dynamics of recurring phenomena with improved time resolution and improved signal-to noise performance.

In another embodiment, both spatial and temporal modulation embodiments noted above can be combined.

The radiation can be comprised of particles selected from the list containing but not limited to photons, electrons, positrons, sub-atomic particles, protons, neutrons, ions, atoms or molecules.

Preferably the sum of radiation intensity measured for all distinct directions is at least 90% of the total radiation intensity incident on the measurement surface.

Preferably the modulator directs radiation into at least three directions.

Preferably the modulator produces cyclic permutations of a base mask with at least two distinct regions.

Preferably the modulator causes each region of a base mask to direct at least half and preferably more than 90% of the radiation incident upon that region into a distinct direction.

Preferably at least one region of a base mask of the modulator directs a portion of radiation incident upon that region into a first direction and at least some of the radiation incident upon that region into a different distinct direction.

In some embodiments at least one region of the modulator is translated or rotated during a measurement such that at least a portion of a base mask region of the modulator passes through at least two measurement regions.

Preferably the fraction of the radiation directed into each distinct direction for each measurement region is calculated as the time weighed geometric fraction that the mask region is directing radiation into that direction.

In some cases the base mask is a Hadamard mask or a pseudo-random mask.

In some cases the spatial modulator produces a cyclic permutation of a base mask and at least a portion of the mask characteristics are determined by motion of the mask during a measurement period. However it is also possible to use non-cyclic permutations, for example where each mask element is individually tunable as in a micro-mirror array. Cyclic permutations arise from masks with fixed geometry.

Preferably at least one element of the modulator has at least two different configurations, such as micro-mirror array, micro-grating, liquid crystal, electro-optical devices.

Preferably each detector output is normalized to the sum of the detector outputs.

Preferably the properties of the radiation to be measured are obtained by multivariate least squares analysis.

Preferably the information in the radiation to be measured is obtained by principle component analysis of the raw detector outputs (as above) or the normalized detector outputs (as above).

In one important feature the radiation pattern with N regions is analyzed by statistical analysis to find a smaller number m of latent variables; making m measurements, and using statistical analysis to infer the value of each latent variable. This feature is useful in circumstances where some of the N regions are correlated and in circumstances where some of the N regions contain little information of interest.

Each latent variable describes a part of the total variance in the underlying N region data set. The user may choose to use only as many latent variables as are required to model the N region data set with an acceptable degree of precision. For example, if the latent variables are found by PCA, the first m latent variables usually describe most of the variance in the underlying N region data set. Empirically, the first three latent variables often describe more than 90% of the variance in an infrared spectrum with hundreds of spectral regions. The user may choose to use three latent variables as an acceptable approximation to the N region data set or choose to use more latent variables to improve the precision of the approximation.

Preferably the total intensity of the radiation summed over all detectors varies for at least some of the spatial modulator configurations; and at each modulator configuration, a raw intensity value is generated at each detector; wherein the total intensity for the modulator configuration is C=SUM (detector intensities di) where the data vector is loaded with the values di'=di/C so that this normalization compensates for changes in the intensity.

In one example the modulator comprises dynamic Toeplitz masks and the resolution is varied by changing the sampling rate.

In one important end use, the radiation is provided by a time of flight mass spectrometer.

In one important end use, the radiation is provided by florescent decay.

In one important end use, the radiation is provided by a flow cell for measuring fluid flow.

In one important end use, the radiation is provided by light reflected from particles under analysis.

In one important end use, the radiation is provided by ultrasound emitted by energized solid material for analyzing density of the material.

Preferably a bandpass filter is useful to limit the range of wavelengths propagating through the detection system and to establish boundary conditions for the analysis system.

Preferably a bandpass filter is used to remove spectral bands with little diagnostic value so that the dynamic range of the detectors is used solely to measure spectral bands of greater diagnostic value.

Preferably a bandpass filter is used to optimize the instrument sensitivity for detection of a particular analyte by weighting the contribution of different spectral bands in proportion to the significance of that band.

According to another aspect of the invention there is provided a method for measuring one or more properties of an incident radiation comprising the steps of:
    collecting the incident radiation to be measured;
    dividing the incident radiation into N packets, each packet containing radiation with a different value of a first property;
    separating said radiation packets temporally or spatially using a temporal or spatial modulator and varying the modulator using a modulation sequence to direct at least N different combinations of incident radiation packets into at least two distinct paths;
    measuring the total intensity of radiation in each path with a detector for each modulator configuration to provide a plurality of detector outputs;
    analyzing the detector outputs statistically to obtain information relating to the properties of the radiation to be measured;
    wherein the radiation pattern with N regions is analyzed by statistical analysis to find a smaller number m of latent variables in a spectrum; making m measurements, and using statistical analysis to infer the value of each latent variable.

According to another aspect of the invention there is provided a method for measuring one or more properties of an incident radiation comprising the steps of:

collecting the incident radiation to be measured;

dividing the incident radiation into N packets, each packet containing radiation with a different value of a first property;

separating said radiation packets temporally or spatially using a temporal or spatial modulator and varying the modulator using a modulation sequence to direct at least N different combinations of incident radiation packets into at least two distinct paths;

measuring the total intensity of radiation in each path with a detector for each modulator configuration to provide a plurality of detector outputs;

analyzing the detector outputs statistically to obtain information relating to the properties of the radiation to be measured;

wherein an intensity of the radiation varies for each of a plurality of samples;

and at each time sample, a raw intensity value is generated at a first detector A and at a second detector B;

wherein the total intensity in the time step is C=A+B where the data vector is loaded with the values a'=A/C and b'=B/C so that this normalization compensates for changes in the intensity.

According to another aspect of the invention there is provided a method for measuring one or more properties of an incident radiation comprising the steps of:

collecting the incident radiation to be measured;

dividing the incident radiation into N packets, each packet containing radiation with a different value of a first property;

separating said radiation packets temporally or spatially using a temporal or spatial modulator and varying the modulator using a modulation sequence to direct at least N different combinations of incident radiation packets into at least two distinct paths;

measuring the total intensity of radiation in each path with a detector for each modulator configuration to provide a plurality of detector outputs; analyzing the detector outputs statistically to obtain information relating to the properties of the radiation to be measured;

wherein the modulator comprises dynamic Toeplitz masks and the resolution is varied by changing the sampling rate.

According to another aspect of the invention there is provided a method for measuring one or more properties of an incident radiation comprising the steps of:

collecting the incident radiation to be measured;

dividing the incident radiation into N packets, each packet containing radiation with a different value of a first property;

separating said radiation packets temporally or spatially using a temporal or spatial modulator and varying the modulator using a modulation sequence to direct at least N different combinations of incident radiation packets into at least two distinct paths;

measuring the total intensity of radiation in each path with a detector for each modulator configuration to provide a plurality of detector outputs;

analyzing the detector outputs statistically to obtain information relating to the properties of the radiation to be measured;

including the steps of estimating the time weighted contribution of each band to the total intensity received by each detector in each measurement and setting the coefficients of the Z matrix to explicitly model the time weighted contributions.

This is functionally equivalent to applying a convolution and the resulting H matrix is not binary and singular even in the single detector case.

As described in more detail hereinafter the arrangement disclosed herein provides a multiplexing method to efficiently measure the properties of a particle flux using an optimal number of detectors.

In one embodiment the particles are photons. In the following discussion the terms photon and electromagnetic radiation and EM radiation are used interchangeably. The method may be used for applications including but not limited to spectroscopy, crystallography, interferometry, imaging and spectral imaging. Collection optics known in the art are used to gather and project at least three (and usually many more) different portions of electromagnetic radiation onto a surface where measurements are to be made and a spatial modulator on the surface directs at least two portions to difference detectors. The portions of radiation may vary by source, polarization, wavelength, phase, or any combination of these.

In another embodiment the particles are neutrons. The method may be used in applications including neutron scattering and neutron diffraction.

In another embodiment the particles are electrons. The method may be used in applications including electron diffraction and electron microscopy.

In another embodiment the particles are protons and ions. The method may be used in applications including mass spectroscopy, ion mobility spectrometry and capillary electrophoresis.

In yet another embodiment the particles are atoms or molecules moving collectively to form a pressure wave. The method may be used in applications including acoustic spectroscopy and acoustic imaging.

An object of the invention is to collect and measure more than 60% of and preferably substantially all of the incident wave or particle flux energy. For illustrative purposes, reference is made here to electromagnetic radiation, but the concepts illustrated also apply to other waves such as but not limited to acoustic waves, neutron waves, electron waves, ion waves, atomic waves and molecular waves. Referring now to electromagnetic waves, the invention includes an optional bandpass filter, a spatial or temporal modulator, two or more detector sets or integrators, a control system, and an analysis system.

A bandpass filter is useful to limit the range of wavelengths propagating through the detection system and to establish boundary conditions for solving equation (3) (see below) by the analysis system. Secondly, the bandpass filter can be used to remove spectral bands with little diagnostic value so that the dynamic range of the detectors is used solely to measure spectral bands of greater diagnostic value. Thirdly, the bandpass filter may be used to optimize the instrument sensitivity for detection of a particular analyte by weighting the contribution of different spectral bands in proportion to the significance of that band as determined by chemometric analysis (for example eigenvectors associated with that analyte). The advantage of this approach is that the dynamic range of the detector sets or integrators is utilized optimally to achieve the best possible precision in the analyte measurement.

In one embodiment, a spatial modulator is stepped through a sequence of configurations by the control system. In each configuration the spatial modulator divides incident radiation into two or more parts with spectral content specific to that configuration and each part is measured using a different set of detectors. In the simplest case, there is a one-to-one correspondence between detectors and parts. In cases where an extended wavelength range is measured, a set of detectors may be used to measure each part. For example, a set could comprise but not limited to a UV detector, a visible light detector, a near-infrared detector, a mid-infrared detector, a microwave detector and a radio wave detector. It is understood that additional optics such as prisms, gratings, bandpass filters, dichroic mirrors, mirrors and lenses are employed to direct each spectral region to an appropriate detector. The intensity or amplitude (with heterodyne means) at each detector is integrated and the result is transmitted to an analysis means. The spatial modulator can divide the incident radiation by transmitting one portion and reflecting one or more other portion(s), or by reflecting two or more portions into different directions. Alternately the spatial modulator can divide the incident radiation by transmitting one portion and refracting one or more portions into different directions, or by refracting two or more portions into different directions. Alternately the spatial modulator can divide incident radiation by transmitting one portion and diffracting one or more portions into different directions, or by diffracting two or more portions into different directions. In general, any combination of transmission, reflection, refraction and diffraction can be used to achieve the purpose of directing different portions of radiation into different directions.

In some embodiments, the spatial modulator and associated optics and detectors are in relative motion with respect to the source of radiation to be measured and the relative motion produces the desired modulation. For example, the image on a spatial modulator in a satellite orbiting the earth moves at near constant velocity with respect to the spatial modulator and the image information is modulated in the same way as if the image was stationary and the modulator was moving. In both cases, the relative motion produces modulation.

Other methods well known to a person skilled in the art can be used to steer non-electromagnetic waves.

In one embodiment as described hereinafter, radiation reflected from a rapidly moving object is collected and transmitted to the entrance slit of a spectrometer. The total radiation received at each time step is different due to changes in the distance and orientation of the object with respect to an irradiation source and collection optics. At each time step, a raw intensity value is generated at detector A (reflection) and detector B (transmission). The total intensity in the time step is C=A+B. The data vector is loaded with the values a'=A/C and b'=B/C. This normalization compensates for changes in the overall signal level.

In another embodiment, the radiation to be measured is incident on one or more detectors for a total measurement time T. For illustrative purposes, the detectors may be photodiodes, which produce photo-electrons via the photoelectric effect. The total measurement time is divided into N intervals. During each time interval, a temporal modulator selects one of a plurality of integrators according to a pseudo-random sequence as discussed below and directs substantially all of the photo-electrons produced during that time interval to the selected integrator. In the simplest case of two integrators A and B, either A or B receives photo-electrons during each time interval and the sum of photo-electrons received by A and B over the period T is substantially equal to the total number of photo-electrons produced by the photodiode over the period T. The measurement process is repeated at least N times with N unique sequences and the number of photo-electrons received by each integrator for each measurement is transmitted to an analysis system.

Turning now to the analysis system, it will be noted that multiplexing is the common element in all of the embodiments noted above. The differences are in the details of implementation. The general multiplex equation is $$y=AZb+e \quad (1)$$

where y is a column vector of observations, A is an instrument function, Z is a matrix of multiplexing coefficients, b is a column vector of particle flux intensities and e is a column vector of residuals due to measurement error or uncertainty. Each row of Z contains the multiplexing coefficients for one measurement at one detector and the corresponding row of the measurement vector y contains the measured value. Each column of Z corresponds to a range of values of the independent parameter. There are no restrictions on the range represented in each column. The range of values represented in each column may be discontinuous and the ranges in each column may represent different fractions of the overall span of independent parameter represented over all columns. The range represented in each column is discontinuous in for the case of measuring latent parameters discussed herein. The ranges represented by the columns of Z may overlap. The multiplexing coefficients in each column of Z represent the fraction of particle flux or radiation within the specified range that is directed on a path to the detector specified by the row. Each measurement cycle includes at least two detectors and two rows of Z. The instrument function in an optical system, for example, is a convolution of the efficiencies of each optical component in the system. For simplicity, consider an ideal system in which the A matrix is taken to be the identity matrix I in the following discussion. The multiplexing coefficients of Z represent the geometry of a spatial modulator or the time slices of a temporal modulator. The residuals (noise) are taken to be uncorrelated in the following discussion. Solutions are known to those skilled in the art for the less common case where the residuals are correlated. There are n spectral intensities and n measurements of different combinations of the n spectral intensities. Z is of dimension n×n and both b and y are of dimension n×1. This special case of Z has the solution $$b=Z^{-1}y \quad (2)$$

If the rows of Z are further Hadamard encoded the Z matrix is commonly termed the S matrix in the literature. The S matrix exists only for particular values of $$n=2^m-1,$$

where m is an integer $\geq 0$. The S matrix has the useful property that the inverse is easily calculated and all of the elements can be reduced to binary code greatly simplifying calculations. The S matrix method uses approximately half (n/2+1)/n of the particle flux. The prior art includes the S matrix method used in tandem providing a theoretical sqrt (2) improvement in SNR due to increased signal throughput.

Equation 1 also describes a linear array of detectors. In this case Z is the identity matrix I. The instrument function matrix A includes terms which describe differences in response between detectors in the array. There are n spectral intensities and n simultaneous measurements made by n detectors.

The invention is a physical embodiment of equation (1) without the simplifying assumptions leading to equation (2). The general case used in the invention is computationally more demanding, but the extra computing is justified by a further improvement in the signal to noise ratio incremental to that which can be achieved by the simpler case described by equation 2. As discussed above, the present invention includes d detectors or integrating devices (d>=2) and also allows the possibility of repeating measurements c times (c>=1).

In the present invention, Z is of dimension ndc×n; y is of dimension ndc×1; and b is of dimension n×1. It should be noted that a minimum of nd (c=1) measurements are needed. It is understood herein that n is the number of measured parameters, which may be latent parameters. In the event that data acquisition is interrupted at a non-integral value of c>1, the data can still be analyzed.

Further, the matrix elements of Z are in general complex numbers rather than integers as in the prior art. It is convenient to consider Z to include the convolution with instrument function matrix A for the following discussion, as the convolution with A generally introduces non-integer elements. Due to dimensions, Z cannot be inverted directly in this case. Instead the spectral intensities b can be estimated with minimal error by using the multiple least squares (MLS) solution to equation (1):

$$b=(Z^T Z)^{-1} Z^T y \qquad (3)$$

For further discussion, it is convenient to define $H=(Z^T Z)^{-1} Z^T$. The covariance matrix $Z^T Z$ is symmetric, which simplifies calculating the inverse. In the general case, calculating the inverse matrix is computationally intensive. It should be noted that if the rows of Z are cyclic permutations of a seed sequence, $Z^T Z$ is always a circulant matrix and thus the inverse can be calculated with a discrete Fourier transform. Other solutions of Equation 1 are possible and may be preferred for large values of N. One alternative approach is to correlate the measurement vector y with known input vectors b to infer the coefficients of the transformation from y to b. This can be done by direct methods and by unsupervised methods such as neural networks. While the MLS method is the preferred method of solving equation 1 for systems of moderate size (N<1024), other statistical methods such as supervised and unsupervised correlation will also work and are within the scope of the invention.

The present invention places few constraints on the form of Z. To measure N wavebands using Equation 3, all that is required is that Z has at least N rows; each waveband is represented in at least one row; each row is unique; and $Z^T Z$ is nonsingular. That is measurements can be made using a convenient form of Z and transformed to another basis for computation. The elements of Z are not limited to integers as in prior art, but may be in general be complex numbers. However in most applications the elements of Z are real numbers in the interval [0,1] and represent the fraction of radiation directed to a detector. It should be recognized that multiplying all the elements of Z by a common factor will produce an equivalent result and might be preferred if computations are done on in integer arithmetic for performance reasons. Different choices of Z produce different signal-to-noise ratios in solutions to Equation (3). Z is chosen to balance engineering considerations with minimization of the RMS noise in results calculated from Equation (3). One important class of solutions is built by cyclic permutation of a seed pattern, or base patters for permutations, with at least two distinct regions. As noted above, Hadamard patterns in the prior art are a subset of this category optimized at least in the single detector case to minimize RMS noise. In the scope of the present invention, the Hadamard pattern is extended to two detectors by including the compliment of a Hadamard pattern for the second detector. For two or more detectors, pseudo-random seed sequences can be used as a base for cyclic permutation. For two or more detectors in the scope of the present invention, base seed patterns for each detector can be generated by randomly assigning values between 0 and 1 to each detector for each measurement such that the sum over all detectors is equal to 1 for each measurement. The value assigned for each column represents the fraction of particle flux incident on the corresponding range of independent parameter to direct to the detector specified. The RMS noise can be minimized by a genetic algorithm that iteratively mutates the seed sequences and calculates the RMS noise according to Equation 3.

Another important class of seed patterns is based on Toeplitz patterns, which have a block of Vs and a block of 0's. Physical masks with Toeplitz patterns are generally easier to fabricate than masks based on pseudo-random seeds because the physical size of the regions can be larger.

The elements of Z can also be chosen such that there is no relationship between the rows so as to optimize the signal-to-noise ratio.

In application, y is the measured quantity. y can be written as $$y=y_b+y_s \qquad (4)$$

where $y_b$ is a constant base signal and $y_s$ represents a variable signal. Substituting into (3) we find $$b=H\, y_b+H\, y_s \qquad (5)$$

Since $y_b$ is a constant vector, $Hy_b$ is also a constant vector. Equation 5 indicates that a constant can be added to any input signal y and the only effect is a constant offset in the resulting spectrum b. In hardware, the signal y is usually an analogue voltage (but may be another measurable quantity) that has been offset, amplified and then digitized. The hardware components work within set limits defining the dynamic range of the detection system. Optimally, the dynamic range of the detection system is set to match the range of input signals generated by a sample to be measured. The detection system can be calibrated by performing the following steps.
1. Measure y with zero offset and low amplification for a representative set of samples.
2. Determine the average minimum and maximum signal values and the standard deviation of each for the representative set of samples.
3. Set the minimum expected signal to the average minimum minus three standard deviations.
4. Set the maximum expected signal to the average maximum signal to the average maximum plus three standard deviations.
5. Set the voltage offset to the expected minimum signal.
6. Set the amplification gain g to (detection system dynamic range)/(expected maximum−expected minimum).

In operation, $y_s$ is measured within the dynamic range of the detection system and then digitized. For many applications, the only part of interest is $y_s$. Optionally, the digital value of $y_b$ can be added to restore y.

For many practical applications pertaining to pattern recognition within the scope of the invention, calculating the spectral intensity vector b is not necessary. From equation 3, it is evident that b is composed of linear combinations of y vector elements. The y vector elements, as noted in the normalization procedure above, can be linear combinations of measurements. Any analysis procedure that computes combinations of the spectral intensity b can also be applied to the measurement vector y and will produce an equivalent result expressed relative to a different set of basis vectors. In layman's terms, different sets or basis vectors are just different coordinate systems. For example in three dimensional space, a point can be expressed in Cartesian coordinates as $\{x,y,z\}$ or equivalently in spherical coordinates as $\{r, \theta, \phi\}$. In most practical applications the number of dimensions is larger than three. The analysis procedure can be any multivatiate statistical analysis method such as LDA, MLS, PLS, PCA or propagation methods such as neural networks. For example, a pattern recognition algorithm such as principle component analysis (PCA) conventionally computes linear combinations of the b vector elements which best capture the variance in the data set. Since the b vector elements are themselves linear combinations of y vector elements, it follows that the PCA algorithm can take the raw data y vector as input directly to produce equivalent results.

The arrangement herein is capable of obtaining spectra with different levels of spatial resolution. In the prior art the resolution is fixed by the spatial encoder. In the present invention, the spectral resolution can be increased by increasing the sampling rate. The corresponding code is altered to reflect the higher sampling rate by duplicating entries. For example, the code sequence $\{1001101\}$ becomes $\{11\ 00\ 00\ 11\ 11\ 00\ 11\}$ at twice the resolution. While the resolution can be increased indefinitely by this method, the practical limit is determined by the resolution of the system directing particle flux onto the spatial modulator. The sampling time increases proportional to the resolution: to improve the spectral resolution by a factor of 2 requires twice the sampling time. A Fourier Transform spectrometer has the same time dependence, but there is a requirement to translate the scanning mirror in the interferometer twice as far. The improved resolution in the present invention can be achieved by electronic means alone without altering any mechanical parts. As shown below in FIG. 14 only particular operating parameters provide valid results with enhanced resolution. The resolution of an array detector is fixed. The resolution is improved in a conventional dispersive instrument by reducing the slit width resulting in a loss of throughput. Consequently the sampling time increases as the square of the improvement in resolution. Multiplexing instruments have a clear advantage.

In regard to duty cycle, the arrangement herein can operate in both static and dynamic modes.

In the static mode, the spatial modulator is held in a fixed configuration for the duration of each measurement. For the single detector case, this corresponds to a conventional Hadamard spectrometer in the prior art. In this mode there is a one-to-one correspondence between physical regions of the modulator and divisions of the particle flux.

In the dynamic mode, the spatial modulator is in relative motion with respect to the spatially variable particle flux to be measured. The relative motion causes a one-to-many relationship between divisions of the particle flux and physical regions of the modulator. The particle flux from each region is directed to different detectors according to the relative time weighted geometric cross sections of modulator regions for each detector during one measurement cycle.

A Toeplitz pattern can consist of two or more sets of spatially distinct regions. Each set of regions is designed to direct substantially all of the EM radiation incident on said region toward a detector, or set of detectors that is exclusive to that set of regions. The means may include one or more optical elements to concentrate EM radiation from spatially separated regions of the set onto a detector. Each set of regions may employ reflection, transmission, refraction or diffraction to direct EM radiation toward a detector or set of detectors.

A transmissive region may be constructed by placing transmissive material in the region or more preferably by placing a slot in the region. A reflective region can be constructed by placing a highly reflective material in the region. The reflective material is preferably a metal such as Al, Ag or Au with high reflectivity over a broad spectral range. A dielectric mirror may offer higher reflectivity over a narrower spectral range. Other materials that provide high reflectivity in the spectral region of interest may be used. The angle of incidence may be varied to provide sets of reflective regions directed toward different detectors. In some embodiments, the reflective regions have plane surfaces and in other embodiments, the reflective regions have curved surfaces for the purpose of concentrating EM radiation at a detector. A refractive region may be constructed by placing a material with a refractive index >1 in the region. The refractive material preferably is generally wedge shaped so that the general direction of EM radiation exiting the refractive region is not parallel to the general direction of EM radiation incident on the refractive region. Refractive regions with different exit directions can be constructed by varying the wedge angle. Specifically, two or more sets of regions can be constructed by using two or more distinct wedge angles. The surfaces of refractive regions may be plane or curved for the purpose of concentrating EM radiation at a detector. A diffractive region may be constructed by placing a diffraction grating in the region. The diffraction grating may be transmissive or reflective. As EM radiation with different wavelengths will fall on spatially separated diffractive surfaces in a set with a common grating period, the set of paths leading to a common detector is a line in theta-Z space. It should be noted a diffraction grating may function as several logical regions because incident radiation is directed into several diffraction orders. The relative intensity in each order can be tuned by modifying parameters such as the blaze angle, groove depth or grating material. Diffractive regions with different exit directions may be constructed by varying the grating period. The diffractive surfaces may be plane or curved for the purpose of concentrating EM radiation at a detector. Reflective and refractive regions as envisioned in the present invention lead to spatial modulators that are intrinsically variable in three dimensions compared with prior designs which are essentially two dimensional. Two dimensional spatial modulators are generally easier to fabricate than three dimensional spatial modulators, but three dimensional spatial modulators can provide superior performance. The diffractive regions option has the advantage of allowing multiple output directions combined with ease of fabrication at the cost of reduced efficiency.

BRIEF DESCRIPTION OF THE DRAWINGS

One embodiment of the invention will now be described in conjunction with the accompanying drawings in which.

DETAILED DESCRIPTION

Figure 1:
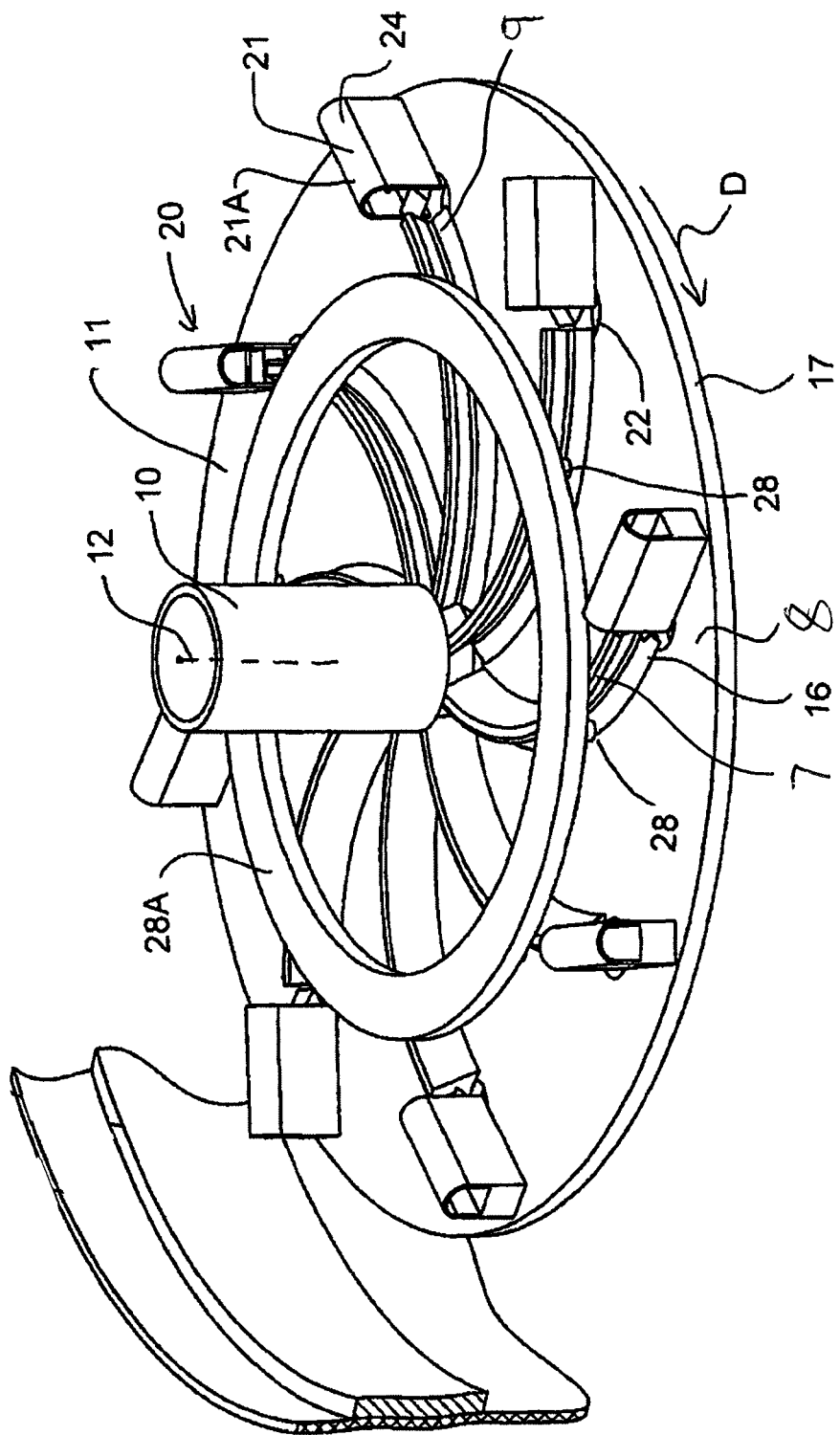
FIG. 1 is an isometric view of a grain sorting apparatus showing one example of an arrangement in which the method according to the present invention can be used.
Figure 2:
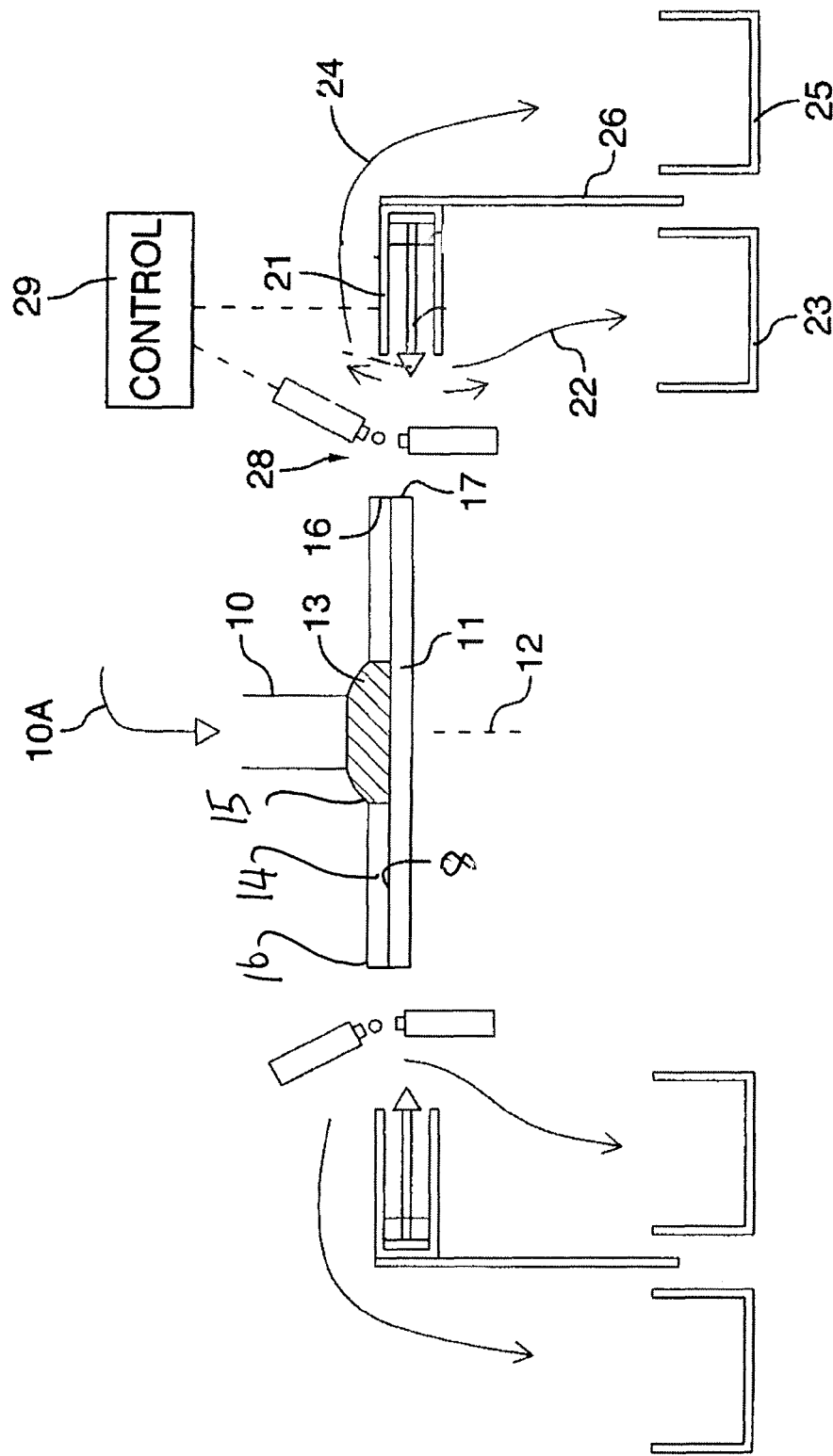
FIG. 2 is a vertical cross-sectional view through the apparatus of FIG. 1.

An apparatus for sorting particles based on a measurable parameter of the particles shown in FIGS. 1 and 2 comprises a supply conduit 10 carrying particles to be sorted from a feed supply 10A which supplies the particles in a continuous stream for presentation through the conduit to a rotary body 11 rotatable around an axis 12. In the embodiment shown the rotary body is a flat disk with the axis 12 arranged vertical so that the disk provides an upper horizontal surface onto which the particles 13 are supplied in the stream from the conduit 10. The conduit is arranged at the center of the disk so that the particles are deposited onto the center of the position where the disk is rotating but where there is little outward velocity. In an exemplary case, the particles may be grain kernels. The kernel velocity at this point is from the flow in the supply conduit 10. The velocity at a point on the disk is v=wr where w is the angular velocity and r is the radius. If kernels are deposited in a region where the change in velocity is too high, they bounce and the flow is chaotic. Kernels are deposited in the central region to minimize the change in velocity.

On the upper surface of the disk forming the rotary body is provided a plurality of ducts 14 each extending from an inner end 15 adjacent the axis outwardly to an outer end 16 spaced at a greater radial distance outwardly from the axis than the inner end. In this embodiment the outer end 16 of the ducts is arranged at the edge 17 of the disk 11. In this embodiment each duct 14 extends from a position closely adjacent the center to the periphery 17 of the disk so that the center the ducts are arranged immediately side by side and the ducts diverge outwardly so that at the outer end 16 they are spaced around the periphery 17.

The inner ends 15 are thus arranged in an array adjacent the axis so that the supply conduit 10 acts to deposit the particles to be sorted at the inner ends 15 of the ducts for entry of the particles to be sorted into the inner ends. As the inner ends are immediately adjacent at the center of the disk, the particles that form a pile at the center which is automatically sorted evenly in to the open mouths of the ducts at their inner ends. Assuming a continuous pile of the particles at the center, the rotation of the disk will act to evenly sort the particles into the individual ducts in a stream defined by the dimensions of the mouth relative to the dimensions of the particles. At the outset of the path along the duct, the particles will be immediately adjacent or overlapping. However passage of the particles along the duct while they are accelerated by the centrifugal forces will act to spread the particles each from the next to form a line of particles with no overlap. As the forces are relatively even, the particles will be evenly accelerated and thus will be evenly spaced along the duct. The kernels align with the duct axially in the first part of the duct and the kernel length defines an initial center to center spacing with some variation due to differences in kernel size. The centrifugal acceleration is uniform at a given radius, but the frictional forces vary by about 20%. The frictional forces scale with the Coriolis force=uN (u=coefficient of friction approx 0.2-0.25, N=normal force to duct wall supplied primarily by the Coriolis force. As set out above, the duct can be shaped to minimize the normal force and friction by curving the duct along the line of net force (mentioned in text earlier).

Selection of the length of the duct relative to the size of the particles can be made so that the spacing between each particle and the particle behind can be selected to be a proportion of the length of the particles. In the example where the separator is used for seeds, the separation between each seed and the next can be at least equal to the length of the seeds and typically 1.5 or 2.0 times the length of the seed. The duct width at the inlet should be about 1.5 seed lengths to avoid clogging.

Thus the ducts are shaped and arranged so that the particles are accelerated as they pass from the inner end to the outer end so as to cause the particles to be aligned one after the other in a row as they move toward the outer end.

The outer ends 16 are arranged in an angularly spaced array at an outer periphery of the rotary body so that the particles of the row of particles in each duct are released by centrifugal force from the disk outwardly from the axis of the disk. The openings all lie in a common radial plane of the disk. The ducts can be formed either as grooves cut into the upper surface of a thicker disk or by additional walls applied on to the top surface of the disk.

An array 20 of particle separating devices 21 is arranged in an annulus on the disk 11 or surrounding the outer edge 17 of the disk so that the individual separating devices 21 are arranged at angularly spaced positions around the disk.

Each separating device is operable to direct each particle into one of a plurality of paths as determined by operation of the separating devices. In the example shown the separating devices are arranged to direct the particles upwardly or downwardly relative to the plane of the outlets 16. As shown in FIG. 2 the separating device 21 can take up an initial intermediate or starting position where the particles are not separated to one direction or the other. The separating device can be moved upwardly so as to direct the particles downwardly into a path 22 for collection within a collecting chamber 23. Similarly when the separating device is moved to a lowered position, the particles are moved upwardly over the top of the separating device along a path 24 for collection within a chamber 25. The two paths 22 and 24 are separated by a guide plate 26 which ensures that the particles move to one or other of the chambers 23, 25.

In order to control the separating devices 21, there is provided a measuring system generally indicated at 28 which is used to measure a selected parameter or parameters of the particles as those particles move from the end of the duct at the edge of the disk toward the separating devices. The measuring system can be, for example, the spectrometer shown in FIG. 3.

In a typical example, the analysis of the particles relates to the presence of degradation of the seed due to disease and this can often be detected optically for example using the systems and disclosed in the prior U.S. Pat. No. 8,227,719 of the present inventor, the disclosure of which is incorporated herein by reference.

Each separating device 21 is associated with a respective detecting device 28, which may include multiple detecting components, operable to measure the parameter of the particles and in response to the parameters measured by the associated detecting device, the respective or separating device is operated to select the path 22 or the path 24.

It will be appreciated that the number of paths can be modified to include more than two paths if required depending upon the parameters to be measured. Such selection to an increased number of paths can be carried out by providing subsequent separating devices 21 positioned downstream of the initial separation. In this way one or both of the paths can be divided into two or more subsidiary paths with all of the separating devices being controlled by a control system 29 receiving the data from the measuring device 28.

The disk 11 thus has a front face 8 facing the supply conduit and the ducts 14 lie in a radial plane of the disk and extend outwardly from the axis to a periphery 17 of the disk 11.

As shown the ducts 14 form channels with an open face facing toward the supply conduit 10. However the ducts may be closed at the top surface with only the mouth 15 and the discharge end 16 open.

As shown in FIG. 1, the ducts 14 are curved so that the outer end 16 is angularly retarded relative to the inner end 15. This forms a side surface of each duct which is angularly retarded relative to the direction of rotation in the counter clockwise direction as shown at D and a side surface on the opposite side which is angularly advanced. This curvature of the ducts is arranged to follow substantially the Coriolis and centrifugal forces so that the particles follow along the duct without excessive pressure against either side wall of the duct. However the shape of the duct is arranged so that the Coriolis forces tend to drive the particle against the downstream side of the duct 14. The sidewall 7 is inclined so that the force F on the particle pushes the particle against the inclined wall driving the particle toward the bottom 9 of the duct 14. This acts to bring all the particles toward the bottom of the duct so the particles emerge from the disk at a radial plane of the bottom surface of the ducts 14.

As shown best in FIG. 1, the ducts 14 are immediately side by side at the inner ends 15 adjacent the axis and increase in spacing toward the outer ends 16. On the inner ends 15 the ducts are immediately side by side so that the maximum number of ducts is provided by the maximum number of openings 15. The number ducts can be increased, in an arrangement not shown, where the ducts include branches so that each duct divides along its length into one or more branches.

In another arrangement not shown the ducts can be stacked one on top of another at the inner ends 15 to increase the number of the duct openings at the inner end. That is for example, if three rings of ducts are stacked one on top of another, the total number of ducts can be increased threefold. The ducts then are arranged in a common radial plane at the outer ends by the uppermost ducts moving downwardly when space becomes available at the outer edge to accommodate the three rings of ducts in a common plane. In this way the outer ends 16 of the ducts can be arranged directly side by side on the periphery 17 of the disk.

Figure 3:
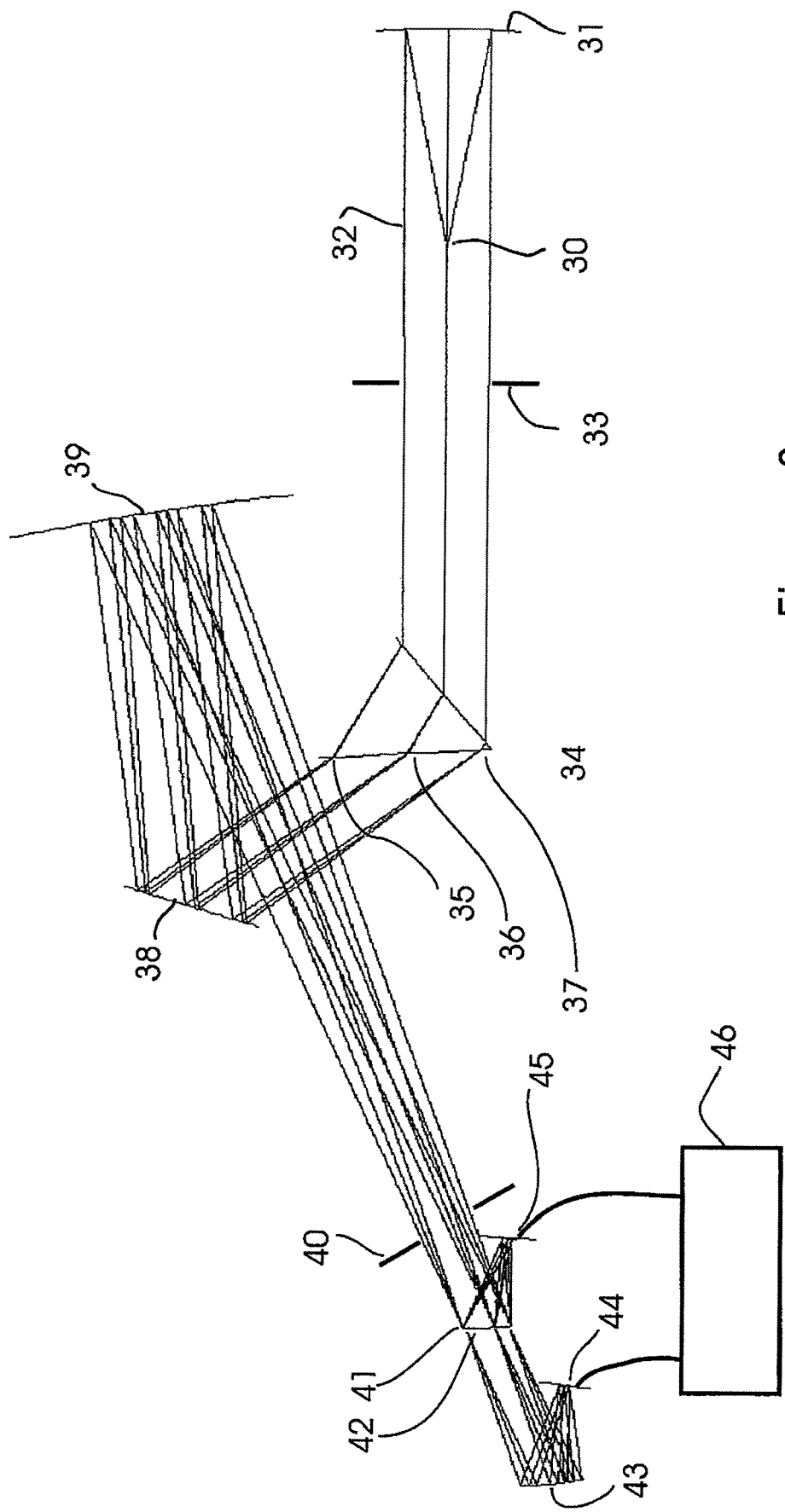
FIG. 3 is a schematic view of a two detector arrangement according to the present invention of the measuring system 28 of the apparatus of FIGS. 1 and 2.

In the embodiment of FIG. 2, the detection device 28 and the separating device 21 are both located beyond the periphery 17 of the disk. In this way the particles exit the peripheral edge 17 and are unguided as they pass from the outer end of the ducts to the array of separating devices. The particles travel along a trajectory determined by the angular velocity of the disk 11 and the direction of the duct 14 at the outer end 16. The associated detecting devices 28 are located relative to the separating device 21 to act on the particle in its trajectory. That is, the trajectory is arranged in the free space between the outer periphery 17 and the separating device 21 so that a particle exiting the discharge end 16 of a duct travels past one of the detecting devices 28 depending upon its position of release and from that detecting device the particle moves to an associated separating device 21 which acts to separate depending upon the analysis carried out by its associated detecting device 28. It is necessary therefore the trajectories are consistent and ensure that the particle that is detected is moved to the requisite separating device In one embodiment as shown in FIG. 3, the invention is used as the detection means in a dispersive spectrometer for example for analyzing the light received by reflection from the samples in FIGS. 1 and 2. The electromagnetic radiation or in this case light to be analyzed is collected and directed through an entrance aperture 30. Usually, but not necessarily, a collimated beam 32 is produced by focusing optics using methods well known to those skilled in the art such as a concave mirror 31. The collimated beam passes through one or more stops 33 to limit angular divergence and is incident on an array of one or more dispersive elements, which causes a wavelength dependent angular deviation in the beam path. The dispersive element can be refractive or diffractive. In the embodiment shown the dispersive element comprises a prism 34. The angular range of deviation is divided into two or more wavelength ranges 35, 36, 37 specified by a minimum wavelength and a maximum wavelength to be measured. For the following discussion, these wavelength ranges are termed 'bands'. Those skilled in the art will recognize that the minimum width of the bands is determined by the resolving power of the preceding optical components. The band widths are not necessarily equal. In a preferred embodiment, the throughput is maximized by using a low refractive index prism 34 for dispersion as the transmission is generally better than 80% over a wide spectral range and there is no spectral aliasing.

In another arrangement discussed in more detail hereinafter, diffraction gratings may be designed to achieve similar efficiency at a specific wavelength, but the efficiency declines with distance from the design wavelength. Preferably the wavelength range for all bands combined is limited between a minimum wavelength and a maximum wavelength. The wavelength range can be limited with a bandpass filter, an aperture stop, or the detector sensitivity.

The dispersed beam is optionally focused by a mirror 38 and a concave mirror 39 and is incident on a first spatial modulator 40 that either transmits or absorbs incident radiation. The first spatial modulator 40 serves as a bandpass filter. In this embodiment the transmitted light is passed to a second surface 41 which contains a second spatial modulator 42.

For each of N measurements, the spatial modulator 42 at the measurement surface 41 divides the incident radiation into a first set of wavelength bands that are transmitted and a second set of wavelength bands that are reflected. The wavelength bands included in each set are different for each measurement so that there are N distinct combinations. Spatial modulator 42 transmits the first set of wavelength bands to a focusing mirror 43 which focuses that set of wavelength bands onto a first detector 44. The spatial modulator 42 is curved to reflect and focus the second set of wavelength bands onto a second detector 45. Although two distinct directions are shown, there may be as many as N−1 within the scope of the invention. The EM radiation intensity summed over all distinct directions is at least 60% of the EM radiation intensity incident on the spatial modulator 42.

The total intensity of EM radiation in each direction is measured with a detector 44, 45 for each spatial modulator configuration and the output of the detector is transmitted to a control system 46 for analyzing the detector outputs statistically to obtain information relating to the spectral properties of the EM radiation to be measured.

Figure 4A:
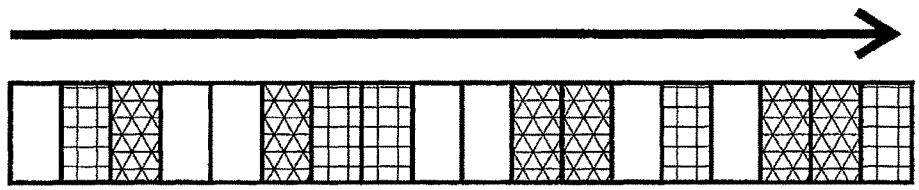
FIG. 4A shows a graph of the different types of region which are arranged in a row to direct radiation incident on different parts of the measurement surface into three directions.
Figure 4:
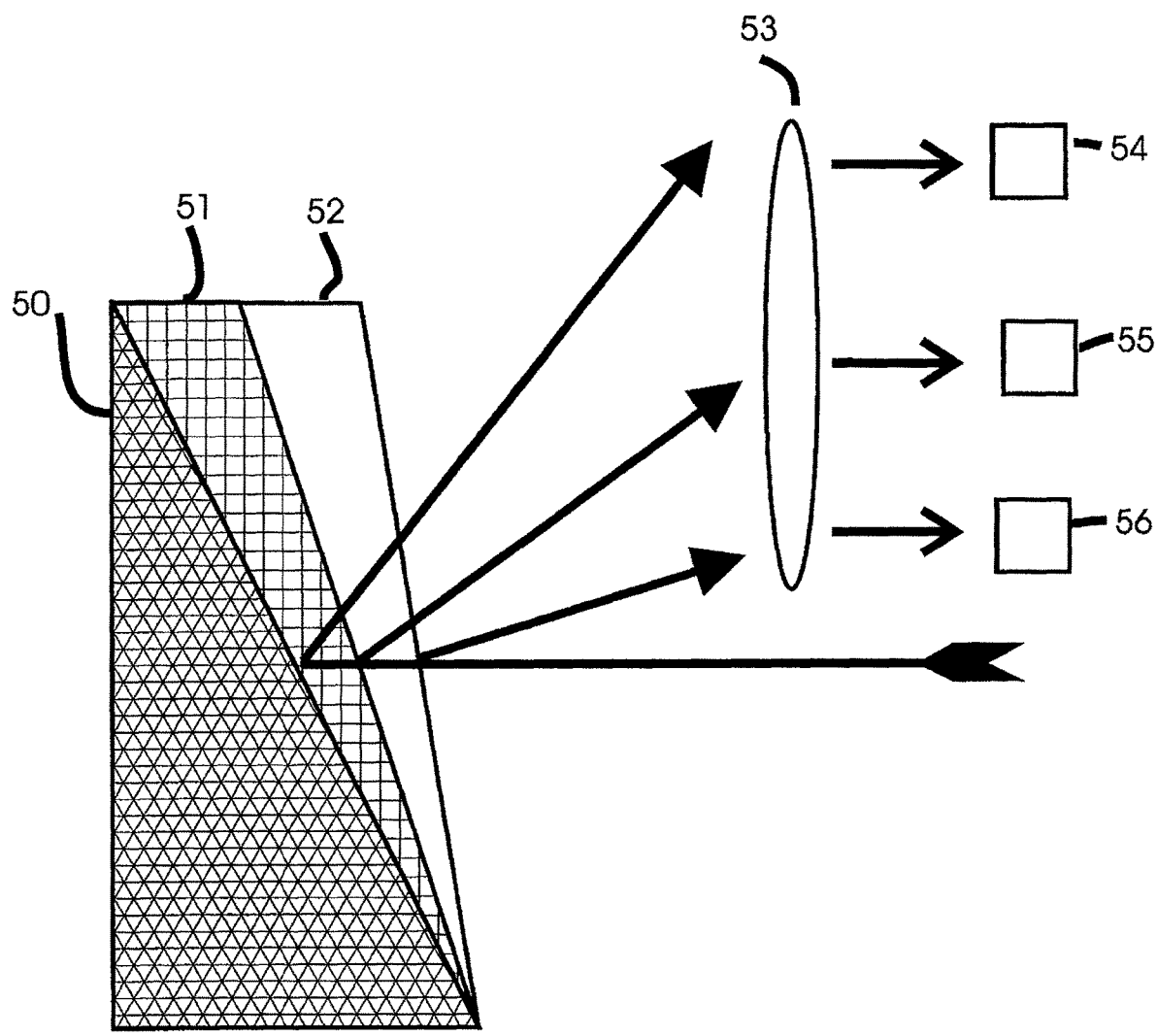
FIG. 4 shows a representative section of a spatial modulator for use in FIG. 3 with three types of reflective regions.

FIG. 4 shows a representative section of a spatial modulator with three types of regions 50, 51 and 52. Each type of region is reflective and inclined at a different angle directing incident radiation to three different directions. A focusing element 53 concentrates radiation onto detectors 54, 55, 56. As shown in FIG. 4A, the different types of region are arranged in a row to direct radiation incident on different parts of the measurement surface into three directions. In some embodiments, the arrangement of regions is two dimensional.

Figure 5:
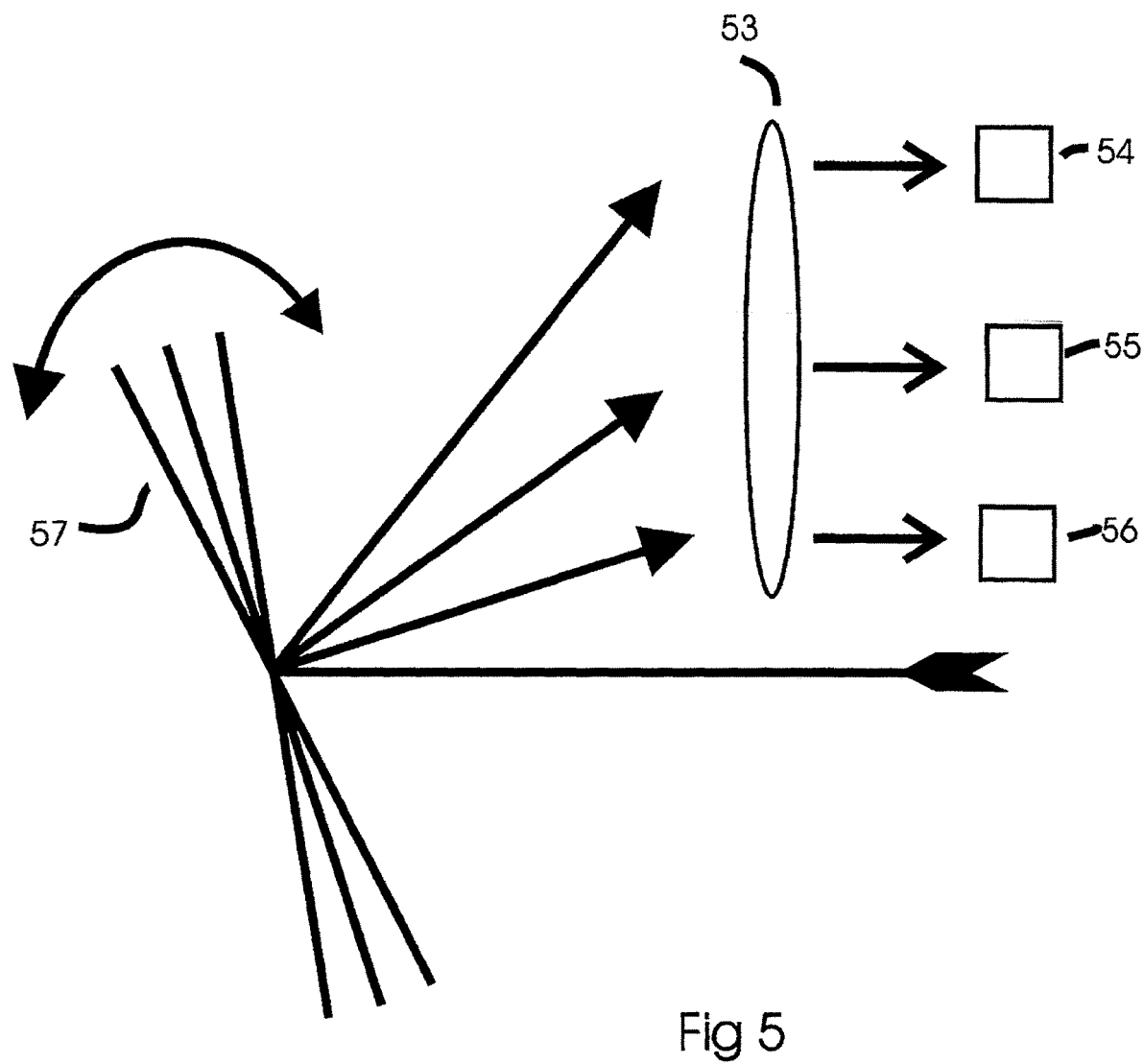
FIG. 5 is similar to FIG. 4, except that fixed mirrors are replaced with a movable mirror that can be switched between three positions.

FIG. 5 is similar to FIG. 4, except that the fixed mirrors 50, 51 and 52 are replaced with a movable mirror 57 that can be switched between many positions with three positions being shown as an example. In a preferred embodiment a micro-mirror array is used.

Figure 6:
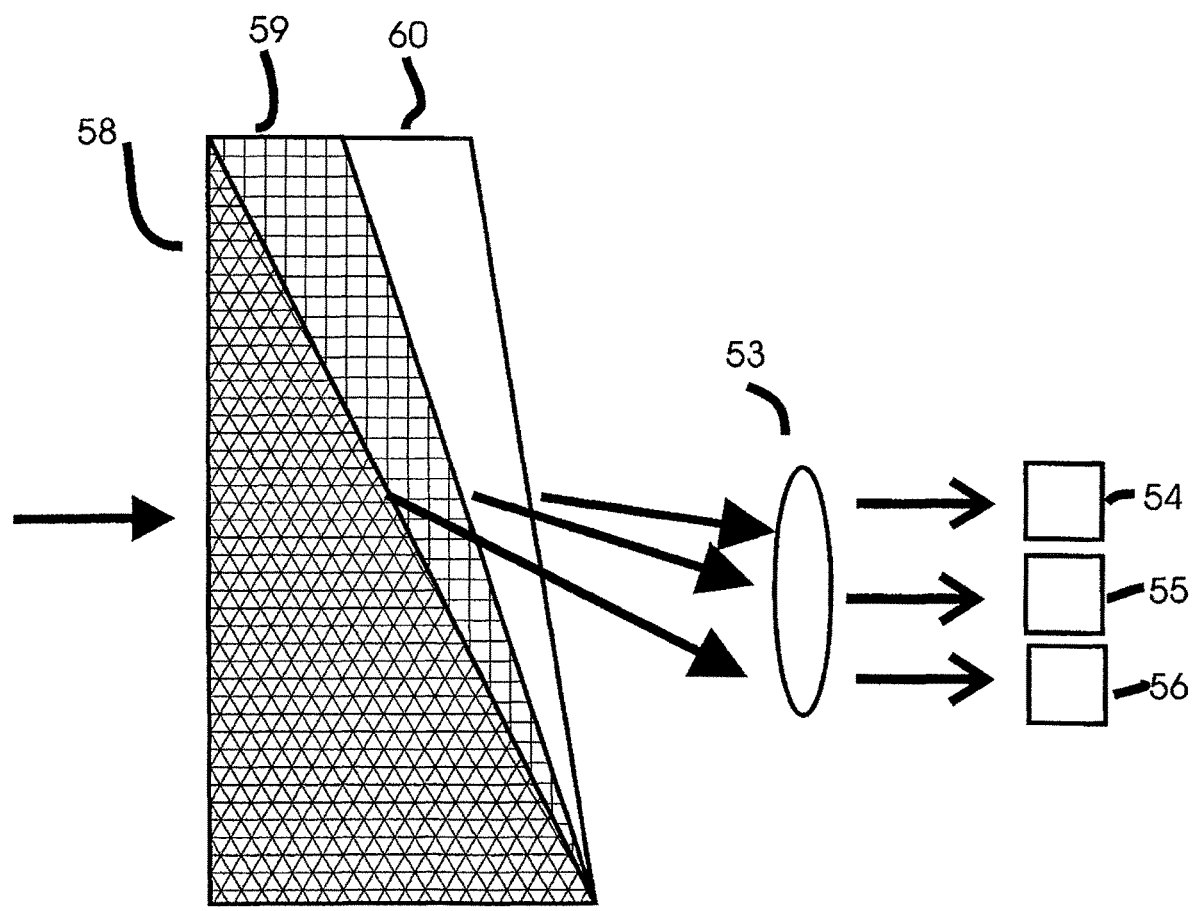
FIG. 6 shows a representative section of a spatial modulator with three types of refractive regions.

FIG. 6 shows a representative section of a spatial modulator with three types of regions. Each type of region has a wedge shaped refractive element 58, 59 and 60 which directs incident radiation into three different directions. Focusing element 53 concentrates radiation onto detectors 54, 55, 56.

Figure 7:
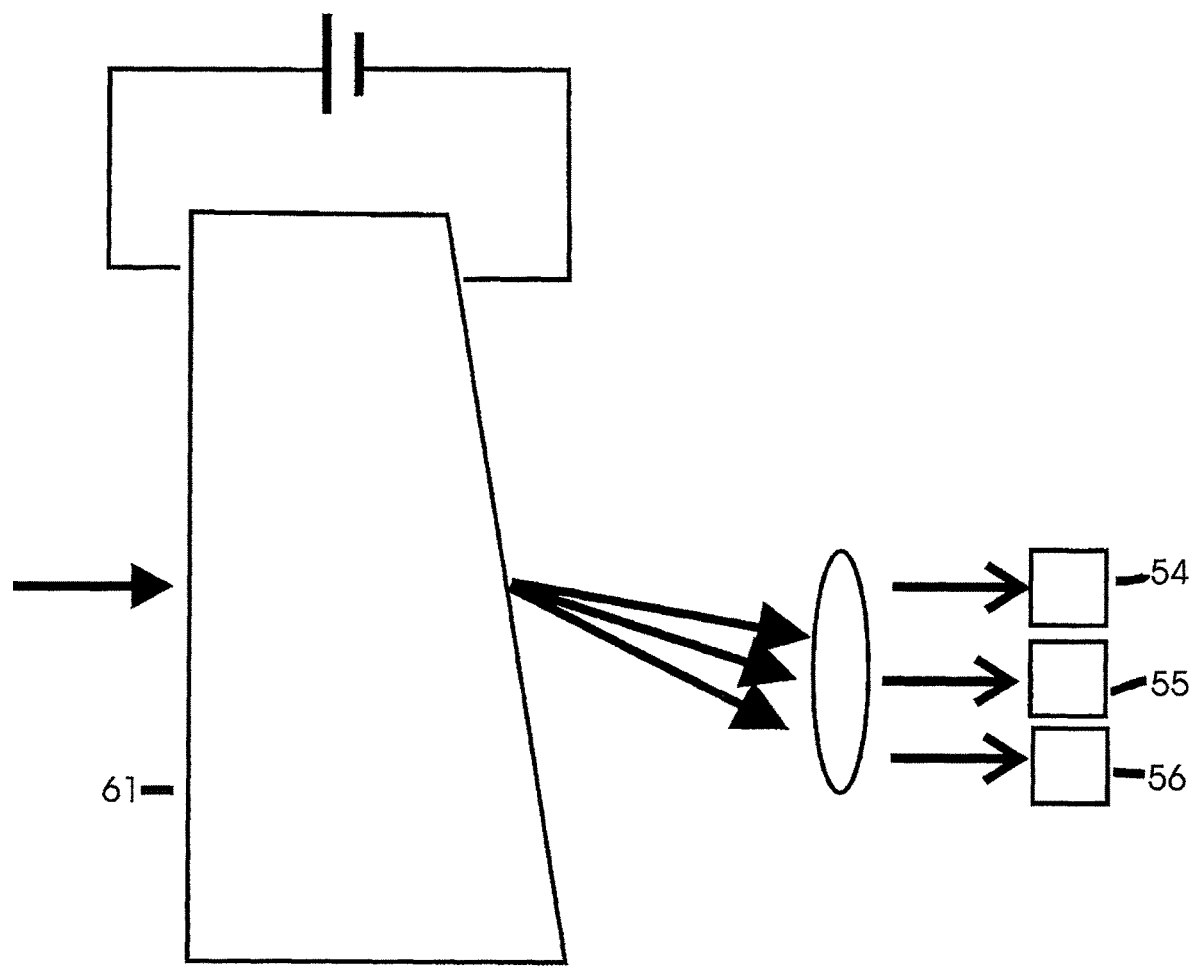
FIG. 7 is similar to FIG. 6, except that a single type of refractive element is used and an electric field is applied to vary the refractive index to direct incident radiation into three different directions

FIG. 7 is similar to FIG. 6, except that a single type of refractive element 61 is used and an electric field is applied to vary the refractive index to direct incident radiation into three different directions. Focusing element 53 concentrates radiation onto detectors 54, 55, 56.

Figure 8:
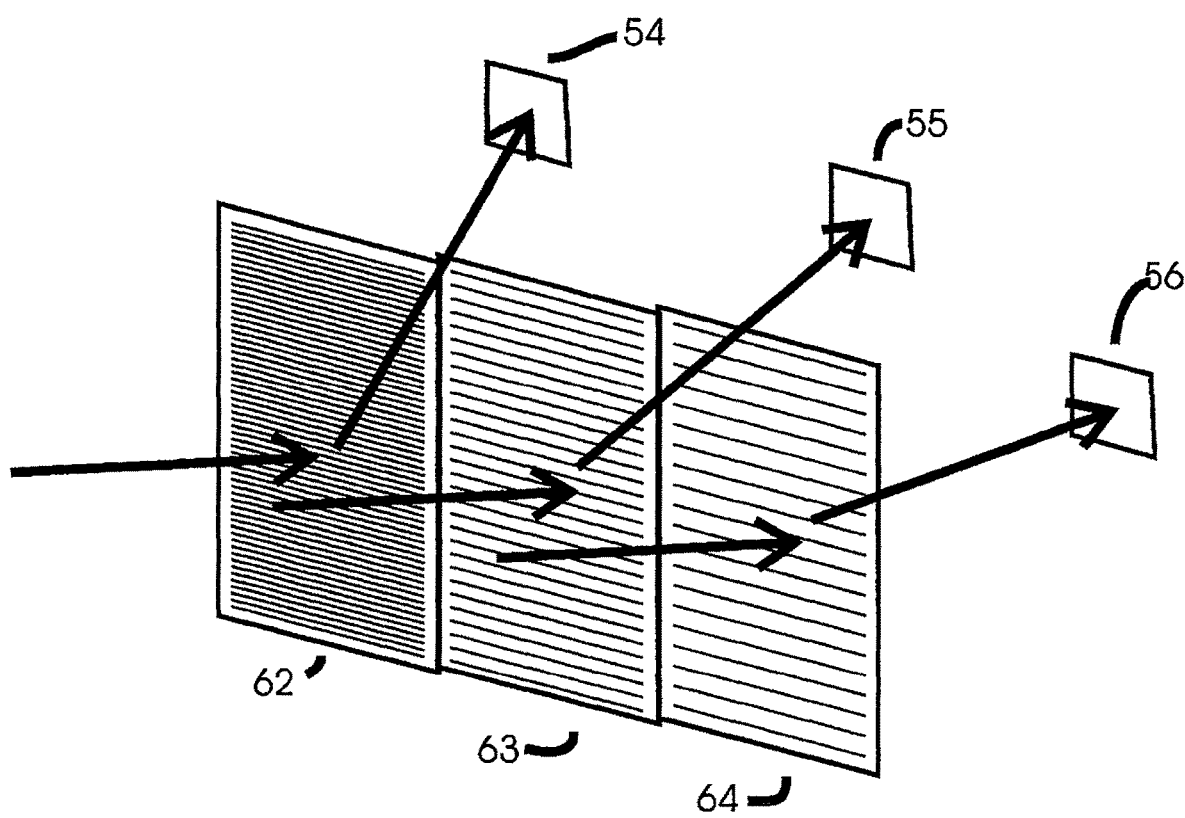
FIG. 8 shows a representative section of a spatial modulator with three types of diffractive regions.

FIG. 8 shows a representative section of a spatial modulator with three types of regions 62, 63 and 64. Each type of region is diffractive with a different grating period. The grating rulings are preferentially substantially parallel to the direction of dispersion along the array to direct diffracted radiation out of the plane of the spatial modulator onto detectors 54, 55, 56.

Figure 9A:
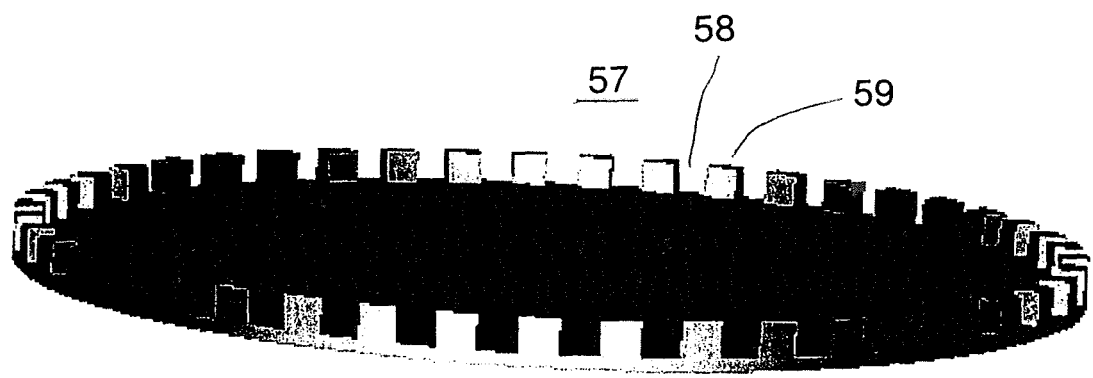
FIG. 9A is a view of a spatial encoder disk with features parallel to the axis of rotation.

FIG. 9A shows a spatial encoder disk 57 with a Toeplitz pattern of gaps 58 and reflectors 59 arranged around the circumference perpendicular to the plane of the disk. The disk rotates about an axis through the center and perpendicular to the plane of the disk. The reflectors are parallel to the axis of rotation. The spatial encoder disk may be used in the spectrometer layout shown in FIG. 3. The spectral bands are brought to a focus over a region equal to one period 48 (FIG. 9B) of gap and reflective regions on the circumference of the encoder disk. As the encoder disk rotates, the waveband regions that are reflected or transmitted change. Conveniently, the curvature of the reflective region can be used to focus reflected wavebands on a detector. The repeating pattern gives cyclic boundary conditions. In other embodiments, patterns shown in FIGS. 4, 5, 6, 7, and 8 can be arranged around the circumference of the disk. A key advantage of this arrangement is that the angular range swept out as the encoder disk rotates is constant over the height of the reflective (or transmissive) region.

Figure 9B:
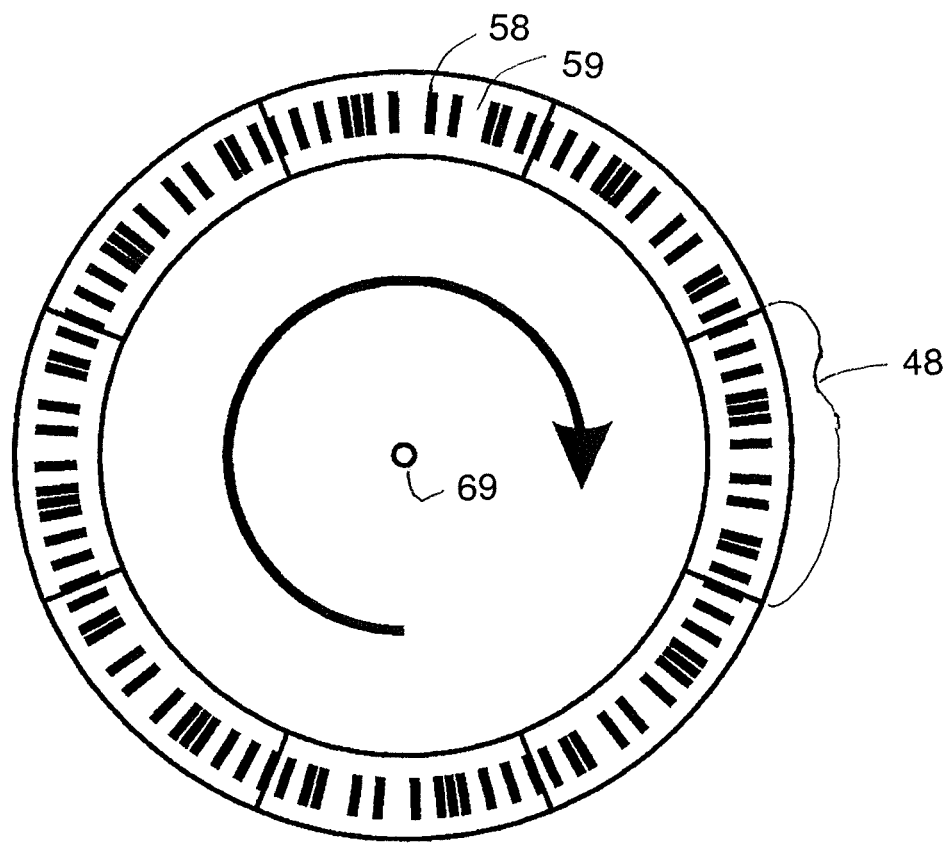
FIG. 9B is a view of a spatial encoder disk with features perpendicular to the axis of rotation.

FIG. 9B shows a flat encoder disk with eight repeating pseudo random patterns. The disk rotates about an axis through the center 69 and perpendicular to the plane of the disk. Wavebands are focused on a region with length equal to one period of the encoder pattern. Radiation incident on a dark region is transmitted and focused on a first detector and radiation incident on a light region is reflected and focused on a second detector. Preferably the disk is fabricated so that the angular range swept out by a reflective or transmissive feature is constant. Alternately, the disk diameter can be made large enough that the convolution introduced by rectangular features is less than a tolerance value. In other embodiments, patterns shown in FIGS. 4, 5, 6, 7, and 8 can be arranged around the circumference of the disk.

Figure 10:
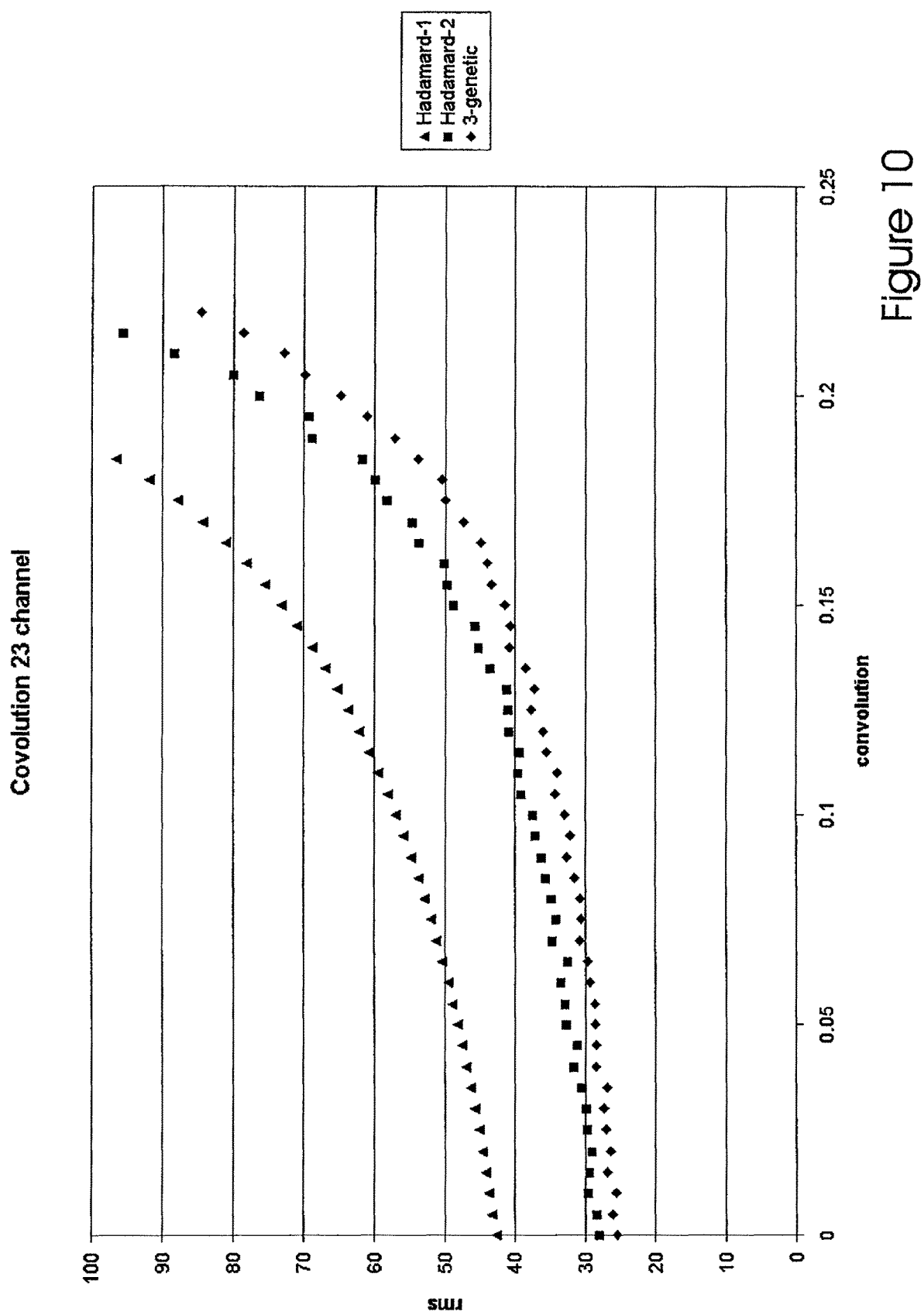
FIG. 10 is a graph of RMS noise v convolution based on a numerical simulation using the arrangement shown in FIG. 3 for 23 channels and three sampling models.

FIG. 10 shows a numerical simulation of the effect of convolution on the RMS noise for 23 channels and three sampling models. The RMS detector noise is 100, but the RMS noise in each channel is less due to the multiplexing advantage. The top curve (Hadamard-1) at zero convolution corresponds to the standard Hadamard technique in prior art with one detector measuring half of the incident radiation. At zero convolution, each spatial mask region is aligned and corresponds with a waveband region. For convolution calculations, the spatial mask moves with constant velocity and the center of each spatial region is aligned with the center of each waveband at the midpoint of each sample integration period. The scan rate (for a complete spectrum) is proportional to velocity. A high convolution factor corresponds to a high scan rate. The convolution index represents the fraction of radiation received by the mask region from each of the wavebands preceding and following the central waveband. The maximum value of 0.25 means that ¼ of the radiation directed by the mask region comes from the preceding waveband, ½ comes from the central waveband and ¼ comes from the following waveband. With convolution applied, the encoding pattern is neither binary nor orthogonal. A multiple least squares algorithm can be used to solve the resulting system of equations. The multiplex advantage declines with increasing convolution and is lost entirely near convolution factor 0.19. The middle curve (Hadamard-2) uses the same Hadamard encoding as a base, except that the compliment of the base encoding is measured with a second detector. The second curve is at a constant ratio of 0.65 to the top curve with a standard deviation of 0.01. A factor of sqrt(2) (0.71) is expected due to the increase in the fraction of intensity measured alone. The further improvement of 0.06 is due to the complimentary mask. The bottom curve (3-genetic) is a three detector encoding identified with a genetic algorithm. A starting point for the genetic algorithm was generated by placing a binary 1 at one in one position selected randomly for each of 23 triplets and calculating by simulation the RMS noise generated by that code. 100,000 random combinations were tested and the best combination was further refined with a genetic algorithm. The genetic algorithm randomly selects one of 23 channels to mutate and then randomly swaps the binary one in that triplet to a different position. If the change reduces the RMS error, the change is kept as the basis for the next mutation. Otherwise the original sequence is retained. The sequences used for the bottom curve are:

$S1=\{0, 0, 1, 0, 1, 1, 0, 0, 1, 1, 0, 1, 0, 1, 0, 0, 0, 0, 0, 0, 1, 1, 1\}$;
$S2=\{0, 1, 0, 1, 0, 0, 1, 1, 0, 0, 0, 0, 0, 0, 1, 0, 1, 0, 0, 0, 0, 0, 0\}$;
$S3=\{1, 0, 0, 0, 0, 0, 0, 0, 0, 0, 1, 0, 1, 0, 0, 1, 0, 1, 1, 1, 0, 0, 0\}$;

For convolution near zero, the RMS noise for the triple detector case is 0.60 of the standard Hadamard case in prior art and 0.91 of the double Hadamard case. The standard deviation is 0.01 in both cases confirming that the triple code advantage is not a statistical artifact. However, the triple code is more robust against convolution than either Hadamard based variant and performs relatively better as the convolution factor increases. The RMS noise is 0.51 of the standard Hadamard and 0.80 of the double Hadamard case at convolution factor 0.22 meaning that the triple code allows both a reduction in RMS noise and a higher scan rate. The zero convolution case was tested by 1000 trial experiments. The total signal strength was approximately 25 volts and the RMS errors were 1.56V, 1.02V and 0.55V for the H1, H2 and S3 cases, respectively. The ratio between H1 and H2 is close to the expected value of sqrt(2). In experiment, the three detector case L3 reduced the RMS noise by more than predicted in the numerical simulation. The degree to which each matched the linear array result L1 was evaluated by calculating dot products between L1 and each of the multiplexing cases. The dot products of H1, H2 and S3 with L1 were 0.971, 0.981 and 0.988 respectively. The match between the linear array spectrum and multiplexing result improves as the number of detectors is increased from one to three.

Figure 11:
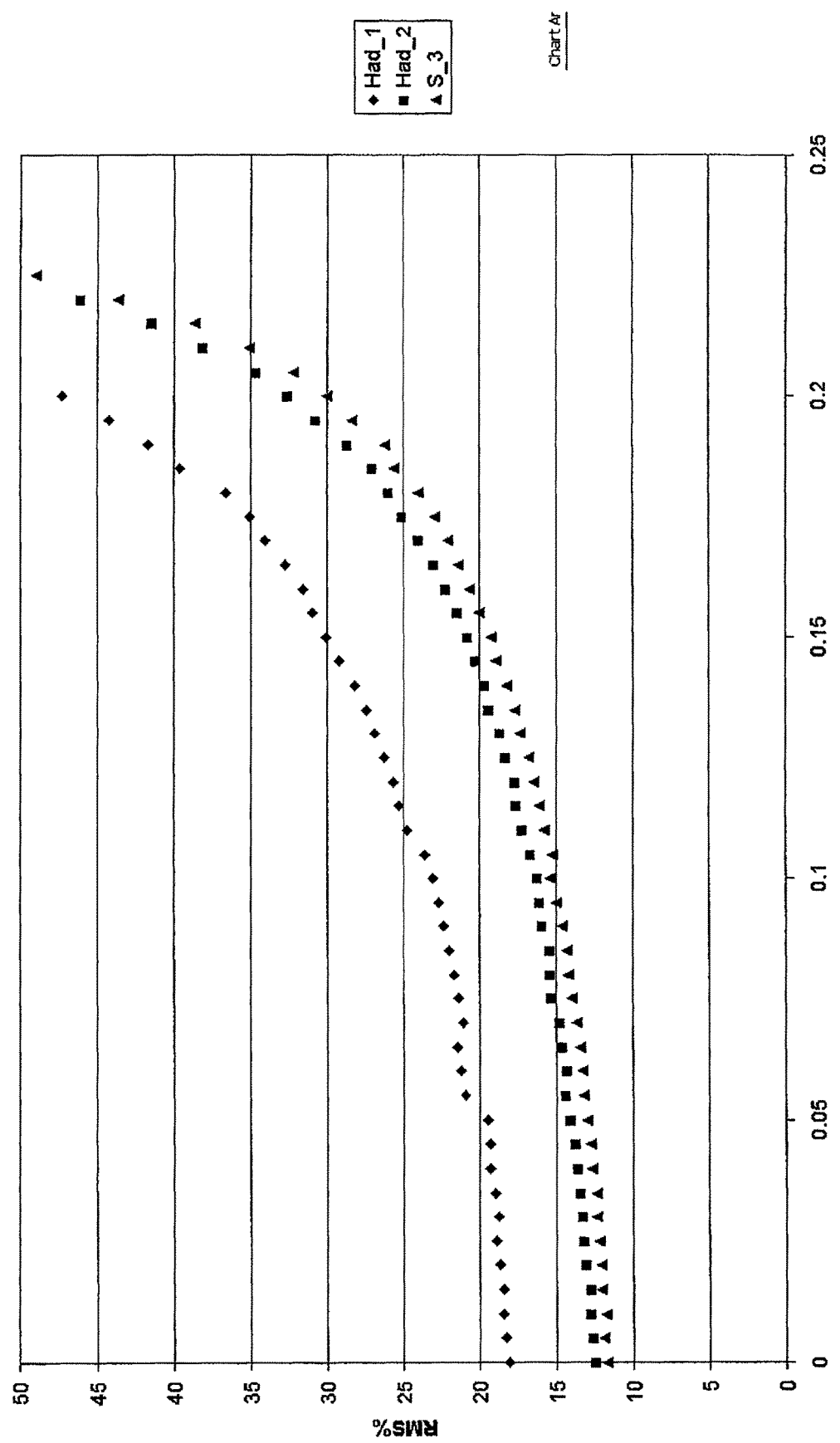
FIG. 11 is a graph similar to FIG. 10, except that the calculation is done for 127 channels which has greater practical application than the 23 channel case.

FIG. 11 is similar to FIG. 10, except that the calculation is done for 127 channels which has greater practical application than the 23 channel case. The overall rank order is the same, and the ratios of relative performance are similar. The three-channel triplet case has RMS noise 0.65 of the single Hadamard case and 0.93 of the double Hadamard case. The standard deviation is 0.01 in both cases confirming that the triple code advantage is not a statistical artifact. Unlike the 23 channel case, there is no trend in the ratio of performance as a function of convolution factor.

Figure 12:
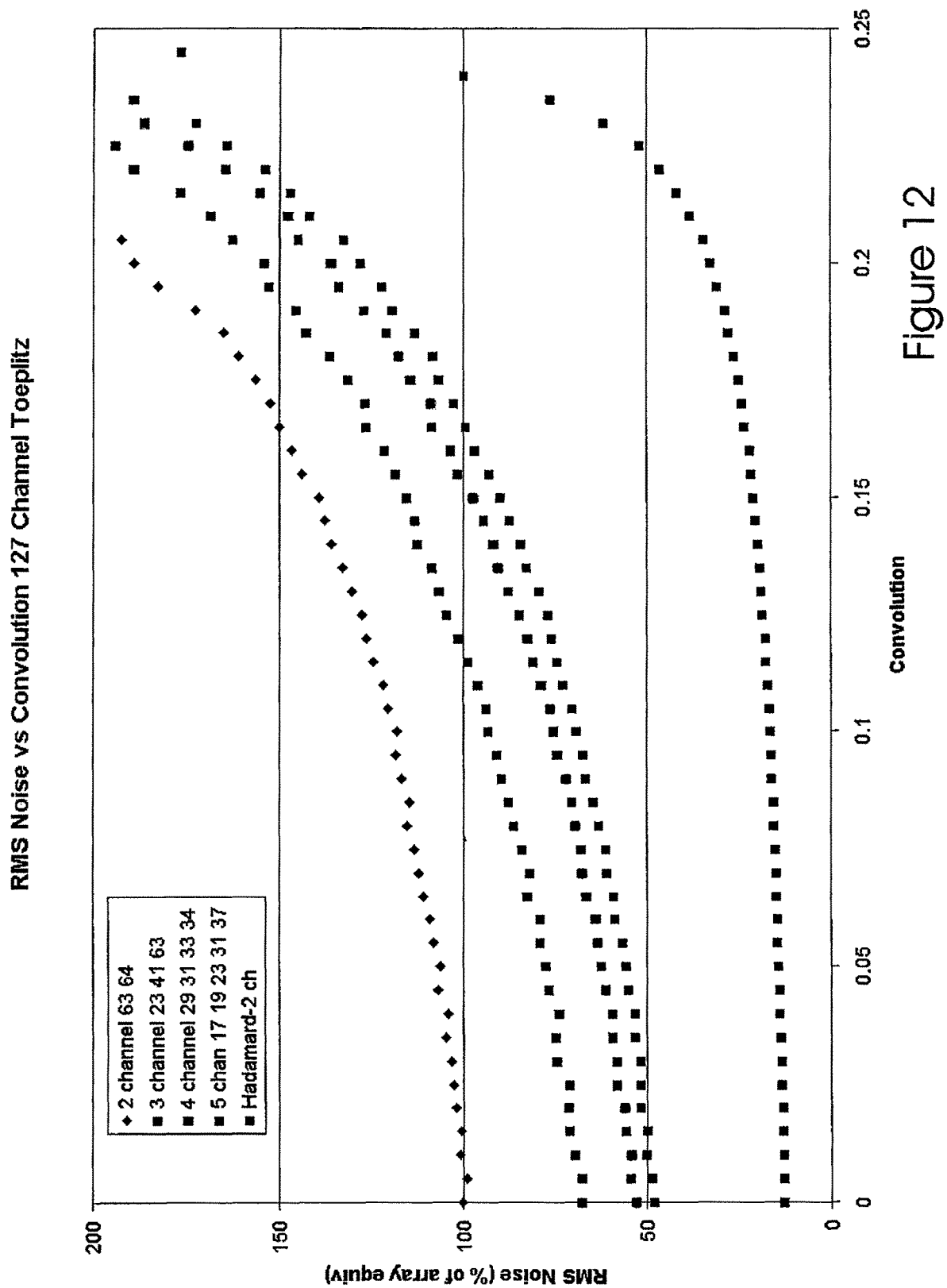
FIG. 12 is a graph of RMS noise v convolution showing the dependence of RMS noise for a 127 channel system as a function of the number of detectors.

FIG. 12 shows the dependence of RMS noise for a 127 channel system as a function of the number of detectors. The top four curves use simple Toeplitz patterns (block symmetric in some literature). The key advantage of Toeplitz patterns is that they are easy to fabricate, possibly resulting in cost savings. A Toeplitz pattern has one contiguous block per detector. The top curve gives RMS dependence on convolution for two detectors. The block sizes are 63 and 64 channels. Except for convolution less than 0.02, the SNR performance is worse than a linear array (RMS=100), but only two detectors are used rather than 127, which is a significant cost saving. The second curve represents a three detector Toeplitz geometry with blocks of 23, 41 and 63 channels. The RMS noise at zero convolution is ⅔ of the RMS noise for a linear array with 124 fewer detectors and remains superior up to a convolution factor of 0.11. The third curve shows the RMS performance of a Toeplitz pattern for four detectors with block lengths of 29, 31, 33 and 34. The addition of a fourth detector further decreases the RMS noise for all convolution factors. The fourth curve shows a five detector case with Toeplitz geometry. The block lengths are 17, 19, 23, 31 and 37. The RMS noise is less than ½ of that of a linear array using 122 fewer detectors at zero convolution. The performance remains superior to a linear array up to a convolution factor of 0.16. The bottom curve gives the performance of a two detector system using a Hadamard pattern. The performance of the Hadamard pattern is significantly better than the performance of any of the Toeplitz patterns, but at the expense of greater complexity in fabrication and alignment during operation.

Figure 13:
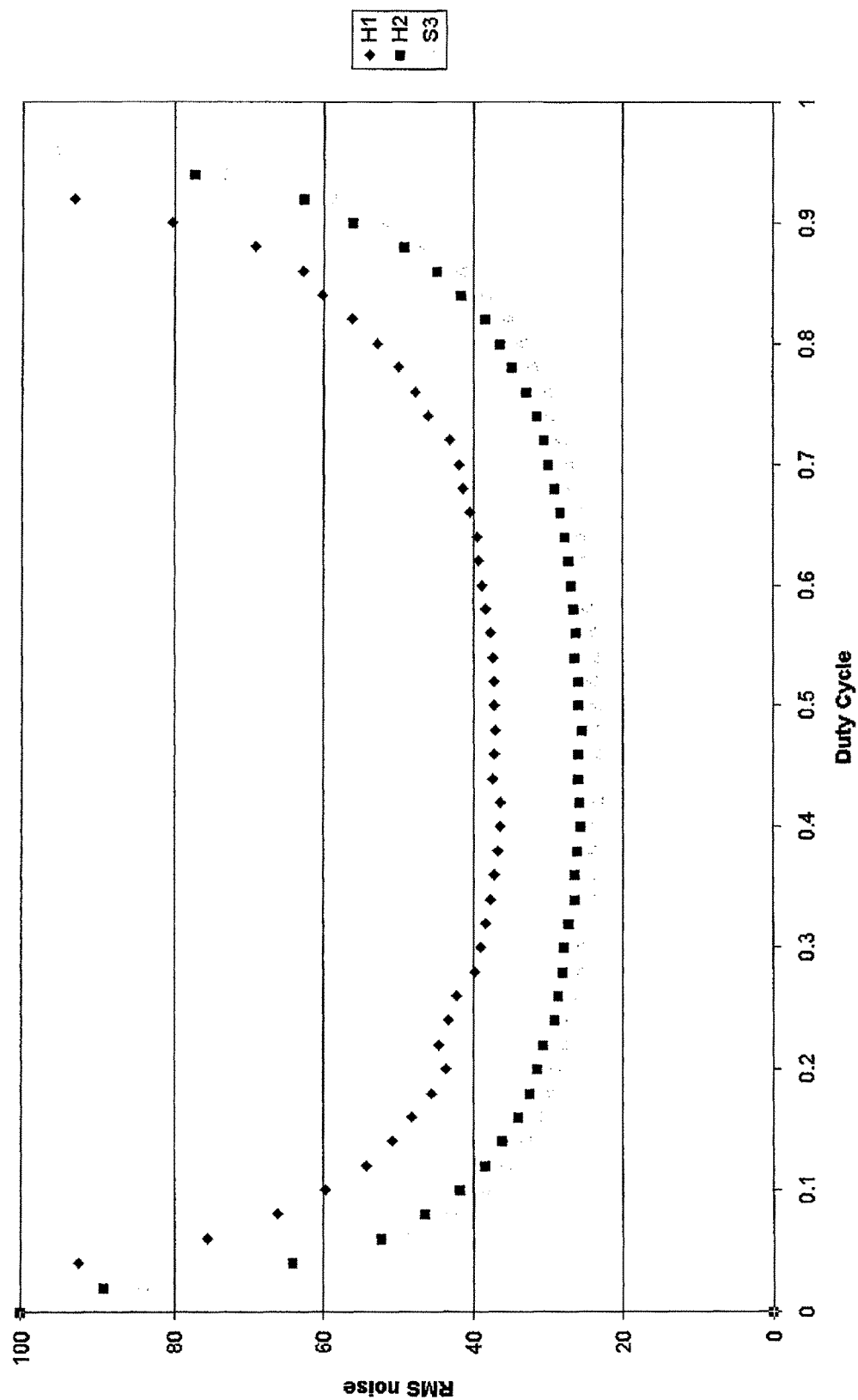
FIG. 13 is a plot of RMS noise vs Duty Cycle for spatial modulator with 127 channels moving at constant velocity.

FIG. 13 is based on the same data as FIG. 10, except that the effect of integration time is factored into the noise calculation. In FIG. 10, the convolution factor can be thought of as a measure of misalignment between the center of a mask region and the center of a waveband region. For a mask moving at constant velocity, the duty cycle is numerically four times the convolution factor. To correct for the effect of integration time, the RMS noise due to convolution is multiplied by $D^{-1/2}$, where D is the duty cycle. The best trade-off between integration time and convolution is in a broad region centered near 0.5 duty cycle for a mask moving at constant velocity. Reducing the mask velocity when the mask and waveband region centers are near alignment and increasing the mask velocity when the alignment is poor can reduce the overall noise. In some embodiments, this can be accomplished with an oscillator undergoing simple harmonic motion.

Figure 14:
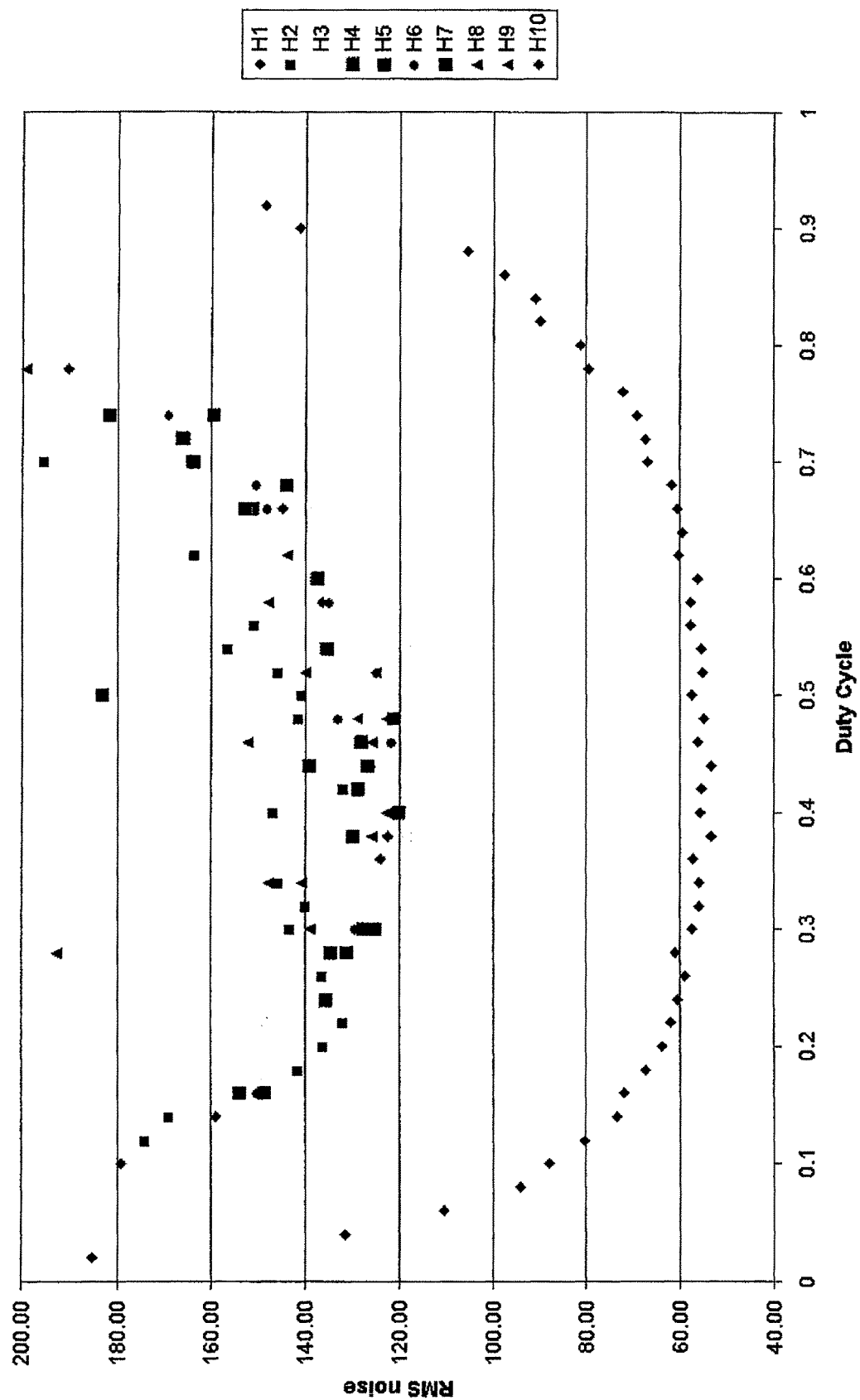
FIG. 14 is a plot of RMS noise vs Duty Cycle for a system with three detectors and 23 channels for the first 10 harmonics of the base sampling frequency.

FIG. 14 shows the effect of increasing the sampling rate relative to the velocity. The base sampling rate is labeled H1 and is associated with Z matrix Z1 with 23 columns corresponding to 23 wavebands. Doubling the sampling rate halves the effective waveband width, so there are 46 wavebands. The number of columns in the Z matrix Z2 is doubled to 46. To make Z2 from Z1, each element in Z1 is duplicated and the duplicate is placed adjacent to the original. Z2 is a singular matrix, but with convolution due to motion Z2 becomes non-singular allowing low noise solutions for some values of the duty cycle. Harmonics for up to ten times the original sampling rate are shown. There is at least one solution for each harmonic that results in RMS noise near 120. For an optical spectrometer, this result means that the sampling resolution can be increased up to the optical resolution of the system with a modest 20% penalty in the SNR without changing the spatial modulator.

Figure 15:
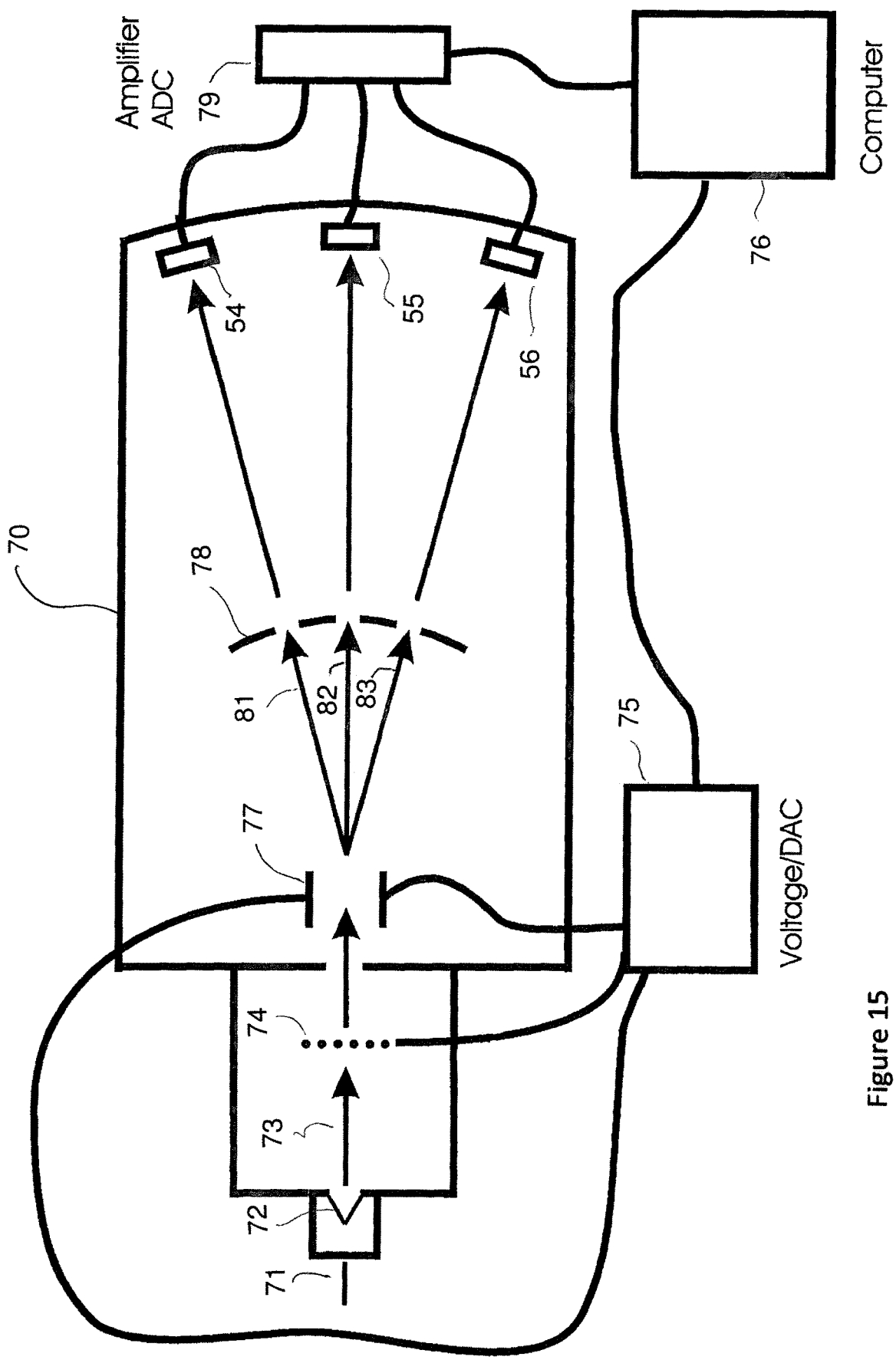
FIG. 15 is a schematic drawing of a time of flight mass spectrometer with three detectors using the invention.

FIG. 15 shows a Multiplexed Time-of-Flight Mass Spectrometer generally indicated 70 according to the current invention. Although the drawing is simplified for clarity, many of the components are similar to the Brock design. Ions are introduced at 71, skimmed at 72, accelerated 73 and collimated (not shown) as before. These steps are not part of the invention. Any suitable means known to those skilled in the art may be used. The ion beam is optionally incident on a Bradbury-Nielsen shutter 74 connected to voltage source 75 controlled by processor 76, which can be used to set the temporal edges of a measurement sequence. This function is analogous to a pre-mask blocking unwanted wavelengths in the dispersive spectrometer described previously. During data acquisition the shutter is open allowing all of the ions to pass. The ion beam is then deflected into discrete angles by voltage applied across one or more sets of deflector plates 77 according to signals received from a controller, which synchronizes data acquisition. In this embodiment the deflector plates form a temporal modulator. This is analogous to changing the refractive index by applying a voltage in the optical embodiment of FIG. 7 above. In the figure three discrete paths 81, 82 and 83 are shown, but the number of paths can be any integer greater than two and less than the number of measurements. The ion beam switches between the between the discrete paths 81, 82, and 83 in accordance with a multi-state pseudo-random sequence designed to minimize the RMS noise and are detected by detectors 54, 55, and 56. Due to the finite voltage slew rate on the deflector plates the ion beam briefly follows paths intermediate between the discrete paths. This is analogous to convolution in the optical case. A mask 78 optionally blocks these intermediate paths. The optional Bradbury-Nielsen shutter 74 may be activated during transitions between voltage states on the deflector plates 77 to briefly divert the ion beam into a stop. More preferably, the discrete paths are arranged such that a transition between any two paths does not cross a third path. In a preferred embodiment, the detectors are arranged in a regular polygon. Ions directed onto a discrete path travel through a field free zone, spread out by mass, and are received by a detector. Detector signals are amplified, integrated, digitized and transmitted to processor 76. The processor computes the charge to mass distribution by multiplying the data vector with the H matrix (Equation 3). Those skilled in the art will recognize that an ion mobility spectrometer can be modified in the same way and realize the same benefit from the invention.

Points of Improvement:
1. The whole ion beam is directed toward one detector at a time and maintains substantially the total intensity to be detected and analyzed. The intensity is greater than 60% of the total and preferably greater than 90% of the total. The prior art divides a complimentary beam between two detectors and the total intensity in the complimentary channels is less than the intensity in the undeflected channel.
2. Including a mask to block intermediate paths reduces stray ions. Stray ions are cited as the key reason why the prior art achieved a 44% improvement rather than the theoretical (sqrt(2)) improvement in the SNR.
3. All of the data channels are analyzed together by MLS rather than individually as in the prior art method.
4. Increasing the number of detectors beyond two as in the prior art increases the multiplex advantage leading to better SNR.

Figure 16:
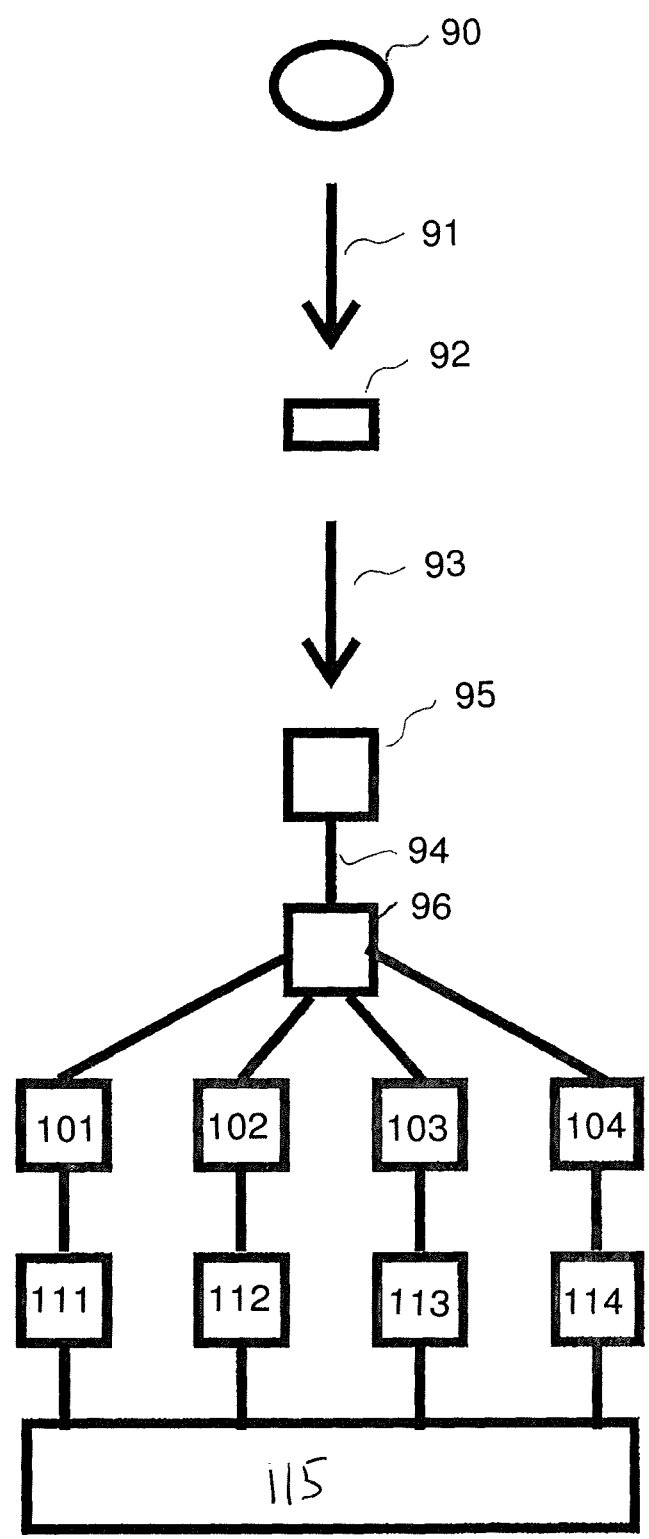
FIG. 16 shows a schematic drawing of a system for measuring fluorescence decay using the invention.

FIG. 16 shows schematic for measuring fluorescence decay. The sample 92 is brought to a starting state and is then irradiated with a pulse of electromagnetic radiation 91 from a light source 90 to produce an excited state that decays via florescent emission 93. The florescent emissions are received for a period T by detector 95, which produces an electrical signal 94 proportional to the photon flux received. The detector may include an amplifier (not shown) to produce a signal proportional to the photon flux. The electrical signal is temporally encoded by a gate 96 at N intervals of length T/N. In each interval the gate directs the electrical signal from the detector to one of four integrating circuits 101, 102, 103, and 104. At the end of each measurement cycle, the integrating circuits are read by an analog to digital converter 111, 112, 113, and 114 and the digitized result is transmitted to processor. In another arrangement (not shown), the integrated signals in integrators 101, 102, 103, 104 are held briefly and directed sequentially to a single analog to digital converter. The sample is allowed to relax to a starting state and the measurement cycle is repeated for N distinct encoding patterns. Processor 115 computes the time dependent florescence with Equation 3.

Figure 17:
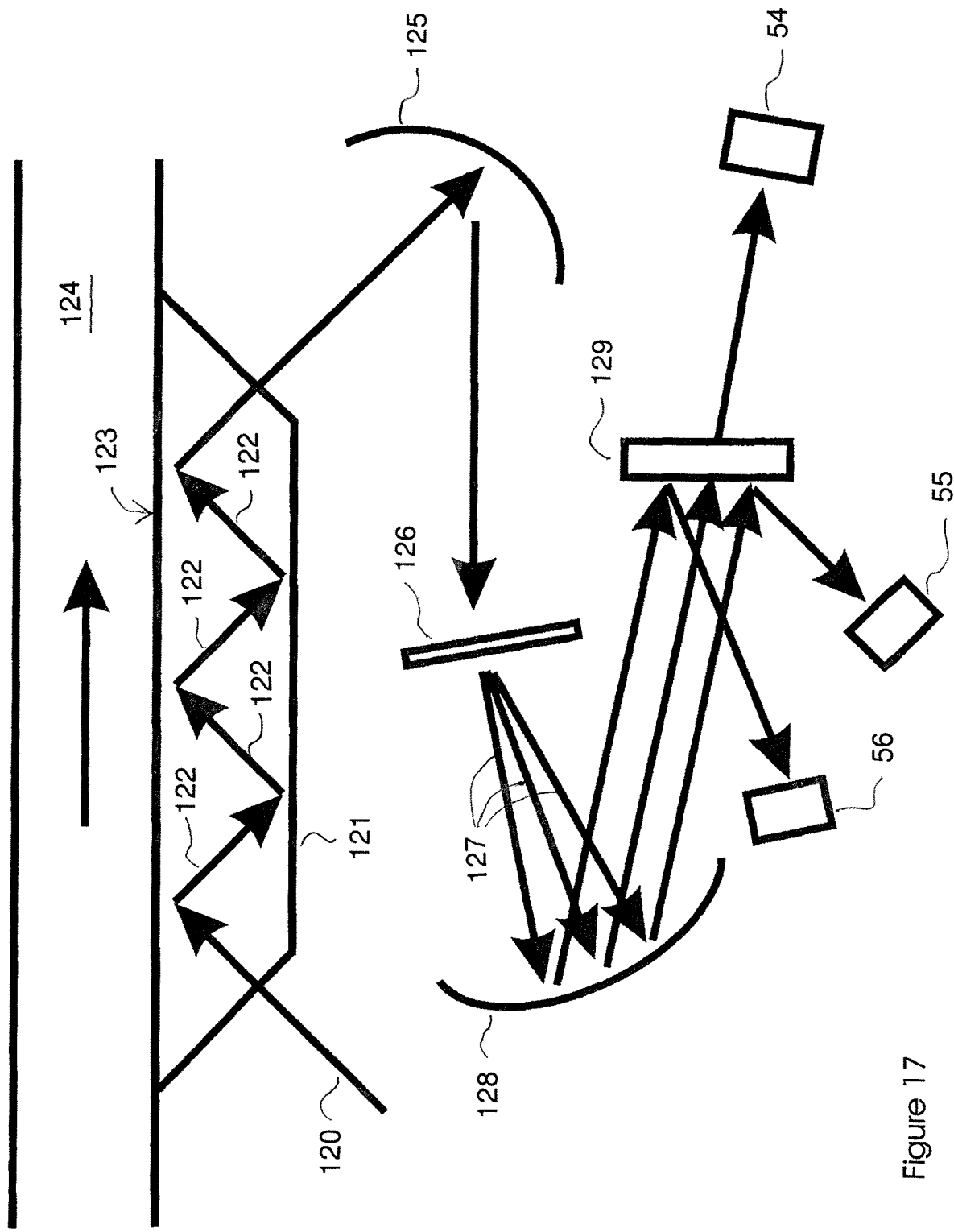
FIG. 17 shows a schematic drawing of a system for a flow cell using the invention.

FIG. 17 shows a schematic of a flow cell for measuring liquid using the invention. In this example, an infrared radiation beam 120 is incident from the left side on a high refractive index crystal 121 (known as ATR in the art) and undergoes several total internal reflections 122 within the crystal before emerging from the right side. The top surface of the crystal 123 forms part of the bottom surface of a channel 124 which contains a flowing liquid to be measured. At each total internal reflection at the crystal/liquid interface, an evanescent wave penetrates the liquid and wavelengths corresponding to vibrational and librational transitions in the liquid are partially absorbed. The modified infrared beam emerging from the right is focused through an aperture (not shown) and collimated by a focusing mirror 125 which directs the infrared radiation through a transmission grating 126. Diffracted infrared radiation 127 is focused by mirror 128 on a spatial modulator 129 which directs different sets of wavebands to three detectors 54, 55, and 56. The spatial modulator cycles through a series of configurations to project N different sets of wavebands to each and the detector readings are transmitted to a processor (not shown) which calculates the infrared spectrum with N spectral regions of the liquid via Equation 3 and analyzes the spectrum to determine the composition of the liquid.

In another embodiment related to PCT publication 2016/0011548 (Prystupa) published 28 Jan. 2016, a piece of meat is made to vibrate with a time dependent pattern by an acoustic transducer and the deformation of the surface is measured by interferometry. Specifically, a quasi-monochromatic light source is collimated and split into two parts with a beam-splitter. One part is directed toward a detection surface and the second part is incident on the meat sample and then directed toward a detection surface. At the detection surface, the parts form an interference pattern in accordance with the optical path difference. The optical path difference at any point is modulated by the acoustic excitation. The arrangement of the present invention is placed in the detection surface to measure time dependent changes in the interference pattern and the changes are analyzed statistically to provide information about the structure of the meat.

In another embodiment, the invention can be used to measure the interference pattern produced by a Fourier Transform spectrometer. The interference fringes for a given wavelength are evenly spaced if interfering beams are collinear and unevenly spaced if the interfering beams are not collinear. The collinear case is mathematically simpler, but uses only half of the available electromagnetic radiation. The non-collinear case herein is preferred despite increased computational complexity because the SNR is improved by using more than half of the available electromagnetic radiation. U.S. Pat. No. 4,797,923 issued to Clarke Jan. 10, 1989 describes a high resolution FTIR spectrometer utilizing partial wave analysis. The invention is a suitable method to measure the high-resolution interference pattern described by Clarke.

In another aspect, the invention can be applied to improve the signal-to-noise ratio and temporal resolution in pump-probe experiments used in many fields including acoustics, spectroscopy, magnetic resonance and crystallography. As an illustrative example, we consider the photon-limited x-ray diffraction experiment described by Yorke in Nature Methods 11(11) 2014 incorporated herein by reference. In the Yorke experiment, x-rays are modulated temporally and the diffraction pattern is recorded by an array of detectors. The temporal evolution of electron density is then calculated by Hadamard inversion (equation 2). The duty cycle in the Yorke experiment is 50%, but rises to 100% by applying methods of the present invention as shown in FIG. 16. In the present invention, the x-ray beam is on for the full duration of the experiment to produce the maximum number of usable photons. The photo-current from each detector is directed to one of m (m>=2) integrating circuits by a gate for each time interval of the experiment such that each integrating circuit receives a temporally modulated flux of photo-current. The gate functionally implements the data collection sequence specified by the Z matrix in equation 3. The length of each sequence is equal to the number of time intervals to be measured n. Each integrating circuit collects photo-electrons for the length of the encoding sequence and then the total charge for each integrating circuit is processed, normally by an analog to digital converting (ADC) circuit, to produce a value proportional to the total charge accumulated by the integrating circuit. The values are entered into the appropriate m positions of the y data vector of equation 3. The sample is allowed to relax to a starting state and the measurement cycle is repeated n times, once for each set of m rows in the Z matrix to produce all mn values of the data vector y. The time sequence for each detector is preferably pseudo random or Hadamard. The electron density at each time step can then be calculated from the diffraction pattern at that time step.

The invention is a method for measuring a dependent parameter as a function of one or more independent parameters where the dependent parameter is a measurable property of a particle flux and the independent parameter(s) are spatial and temporal parameters. For illustrative purposes a general independent parameter is designated x and the dependent variable designated as f(x) varies with changing x. For example, x can be the position on the focal plane of a camera and f(x) is the intensity of illumination received at said position x. In many cases several dependent parameters are measured and then correlated with one another. For example, light incident on a prism is spread into different wavelengths f(x) at different locations x on a measurement surface. The intensity of light is also measured at the same locations and the measurements are correlated to give a spectrum as intensity as a function of wavelength. For the purpose of this document, any reference to a dependent parameter in the context of an independent parameter is to be interpreted as a reference to the underlying correlated spatial or temporal parameter. That is the reference to wavelength in the example above is to be interpreted as a reference to the spatial parameter the wavelength is correlated with. The particles can be of any type including but not limited to sub-atomic particles, protons, neutrons, electrons, positrons, photons, atoms, ions and molecules. The measurable property can be of any type including but not limited to mass, energy, charge, spin, frequency, wavelength, polarization, electric dipole moment, magnetic dipole moment, momentum, pressure and velocity.

The independent parameter is divided into a series of ranges specified by a starting and ending value of the parameter x. Each range is assigned a unique label. It is often convenient to label the range with the average value of x in the range, but this is not necessary and other labeling schemes can be used. For example, a series of ranges could instead be specified by a series of integer indices. The term bin in the text herein refers to ranges.

The invention pertains to a method to measure the value of a dependent parameter in N ranges by making at least N different sets of measurements to produce N sets of scalar parameters. There are P measurements in a set where P is greater than or equal to 2. Each measurement in a set is associated with a weight function wij(x) with values ranging from 0 to 1 where the index i has M values and the index j has P values and M is greater than or equal to N. There are P logical detectors making measurements, one for each value of j. Each measurement is made by multiplying the dependent parameter to be measured f(x) by wij(x) and integrating over all values of x included in the ranges to produce set of scalars gij. The weight functions wij(x) are the physical transfer functions of a spatial and/or temporal modulator describing the fraction of the incident particle flux incident at location x is directed on a path to detector j during measurement i. A spatial modulator may, for example consist of an array of mirrors, each mirror corresponding to a different range of independent parameter x. The transfer function is determined primarily by the reflectivity of the mirror. The highest broadband reflectivity technically achievable is about 0.97, so the transfer function in this case would be 0.97. A defining feature of the invention is the requirement that the sum of weight functions over each range of x is greater than 0.60, that is more than 60% of the particle flux incident on each range is directed on a path to one of P detectors.

Figure 18A:
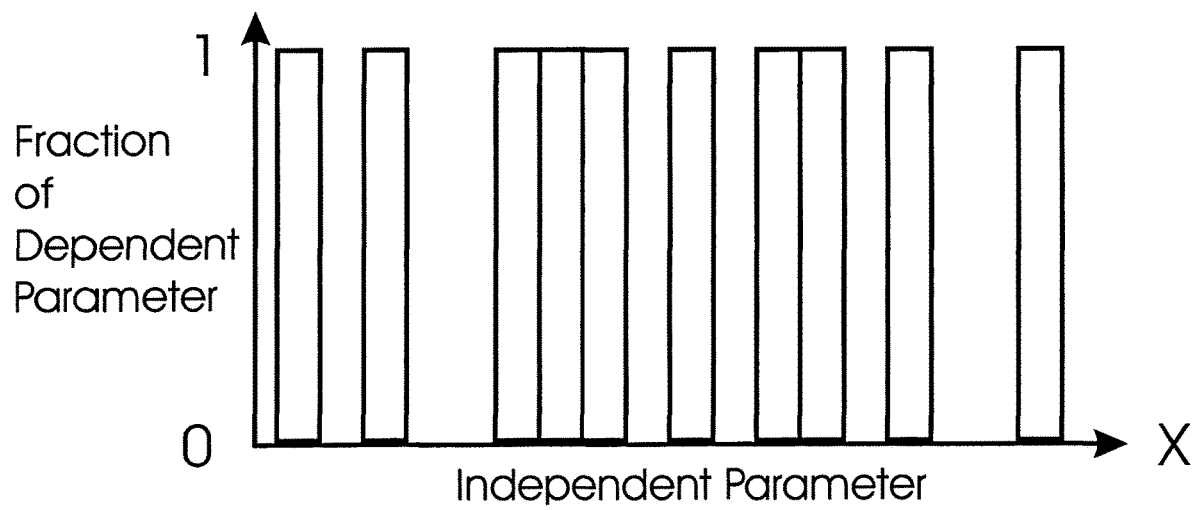
FIG. 18A shows a schematic drawing of a weight function used in the measurement process of the present invention.

FIG. 18 shows the calculation of one measurement schematically. The weight function is shown in (A) is multiplied by the flux intensity (dependent parameter) in (B) and the resulting pieces (C) are summed to provide the integrated flux intensity for the measurement. The weight function 18A is different for each measurement for each detector. In the prior art there is one weight function as shown in (A) that passes about 50% of the incident flux on average to a single detector.

Figure 19A:
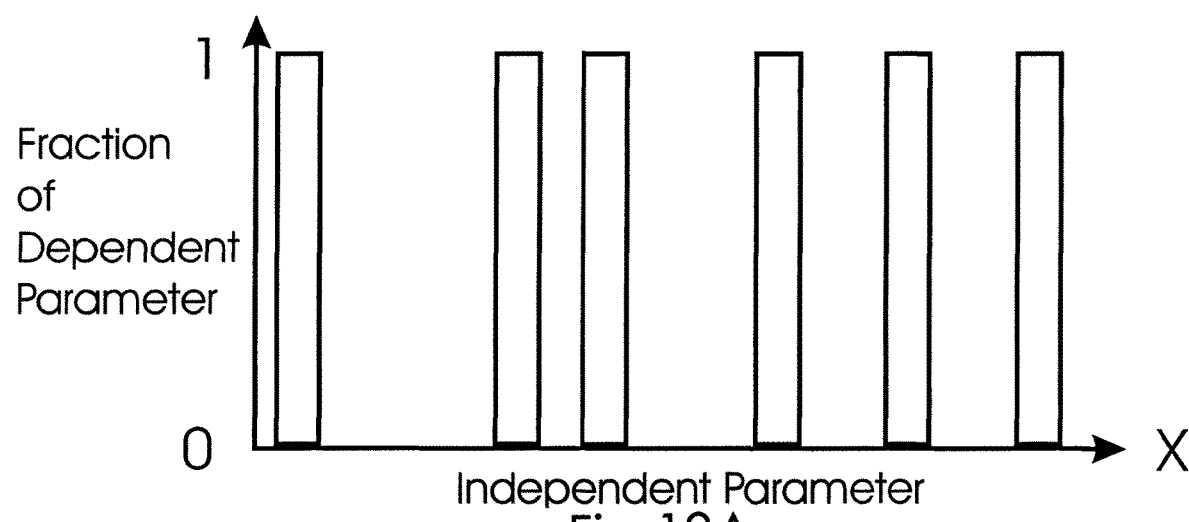
FIG. 19A shows an example weight function of the present invention.
Figure 19B:
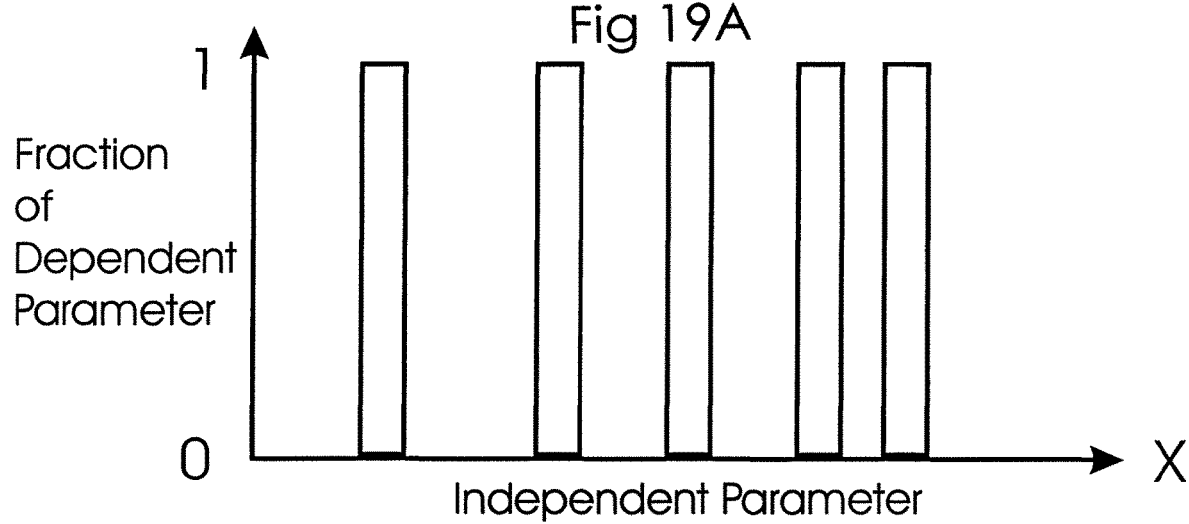
FIG. 19B shows an example weight function of the present invention.
Figure 19C:
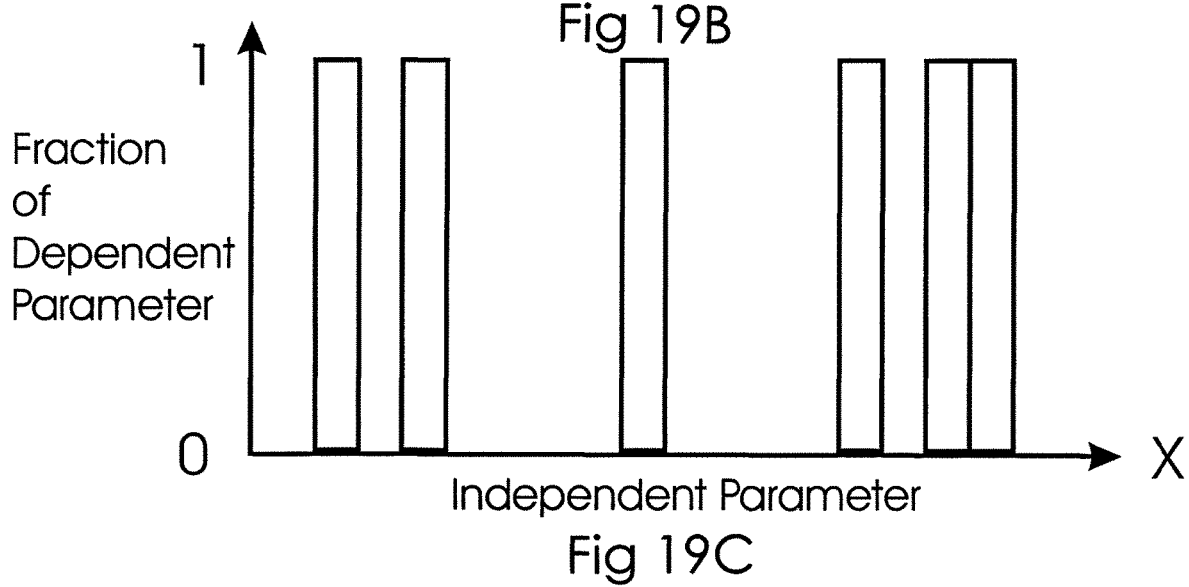
FIG. 19C shows an example weight function of the present invention.

FIG. 19 shows schematic ideal weight functions for an embodiment of the present invention with three weight functions (A), (B), and (C) corresponding to the inputs to three detectors for each measurement cycle. The sum of the weight functions is 1 for all regions of the independent parameter x. In a physical case, the sum of the weight functions is greater than 0.6 and preferably greater than 0.9. For a spatial independent parameter, the weight functions in FIG. 19 can be implemented physically by a set of reflective surfaces as shown in FIG. 4, or by a movable mirror as shown in FIG. 5, or by refractive wedges as shown in FIG. 6, or by changing the refractive index of a wedge with an electric field as shown in FIG. 7, or by a set of diffractive surfaces as shown in FIG. 8, or with a Toeplitz pattern on a rotating disk as shown in FIGS. 9A and 9B. FIG. 16 shows a method to implement the weight functions in FIG. 19 with a temporal independent parameter. In FIG. 16, a pulse of photons passes through a sample suffering refraction and scattering. Photons with different wavelengths emerge from the sample at different times and are registered by a photo detector that converts the photon flux intensity to a voltage waveform. The voltage waveform is directed to integrating circuits in accordance with the weight functions (zero for one of the integrators shown in this example). The integrated voltages are converted to scalar values by analog to digital converters. The light source is pulsed N times. A different set of weight functions is used for each pulse.

Figure 18B:
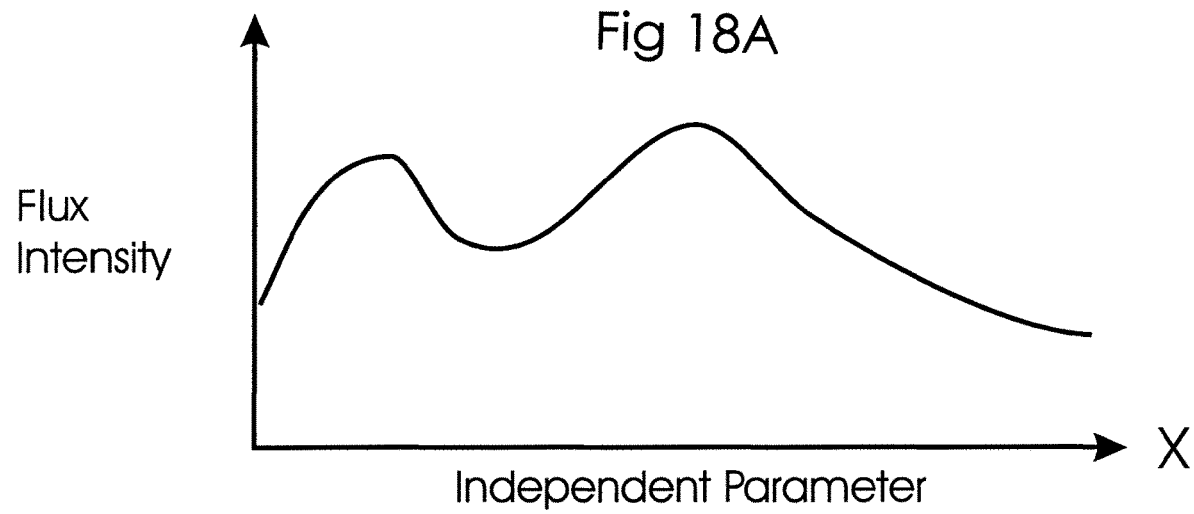
FIG. 18B shows a schematic drawing of a dependent parameter to be measured.
Figure 18C:
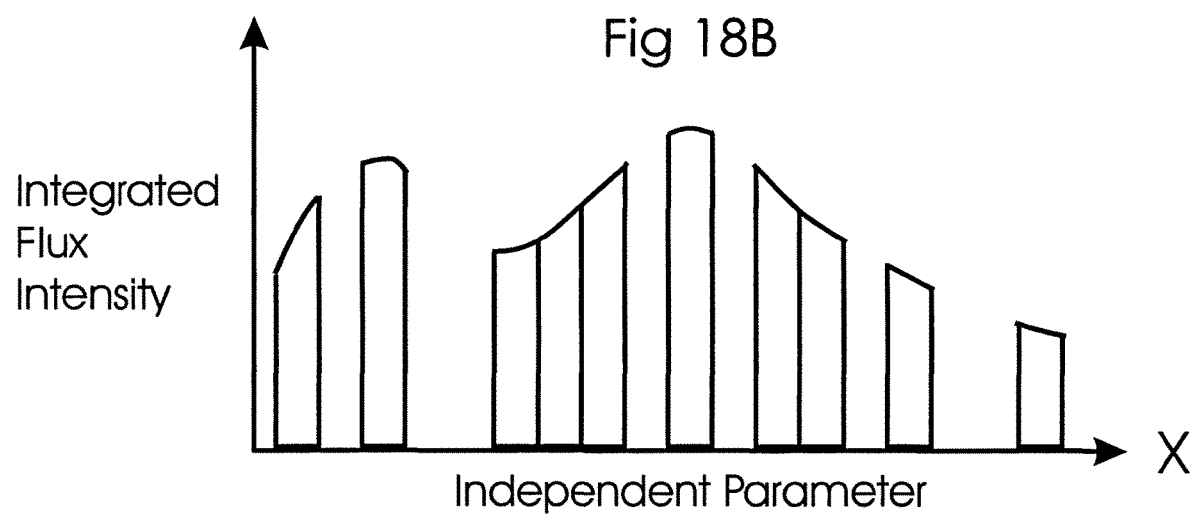
FIG. 18C shows a schematic drawing of the integrated intensity of the dependent parameter in FIG. 18B.

For each set of measurements, the weight functions (A), (B), and (C) in FIG. 19 are multiplied by the dependent parameter as shown in FIG. 18B to produce three separate sums as shown schematically in FIG. 18C. At least N sets of measurements (A), (B) and (C) are preformed to produce at least 3N scalar integrated intensity values in the example of FIG. 19. Note that because the weight functions in this example have constant discrete values over each region, the integration reduces to a sum and the linear algebra solution given in Equation 3 is applicable. Alternately, the system of integral equations can be solved by iterative methods within the scope of the invention. In the context of Equation 3, the 3N weight functions each represent a row of the Z matrix. Each range of the independent parameter corresponds to one column of the Z matrix and the elements in each row are the constant values of the weight functions. The 3N measured scalar values are each loaded into the row of the observation vector y corresponding to the row of the weight function for that measurement.

Figure 20A:
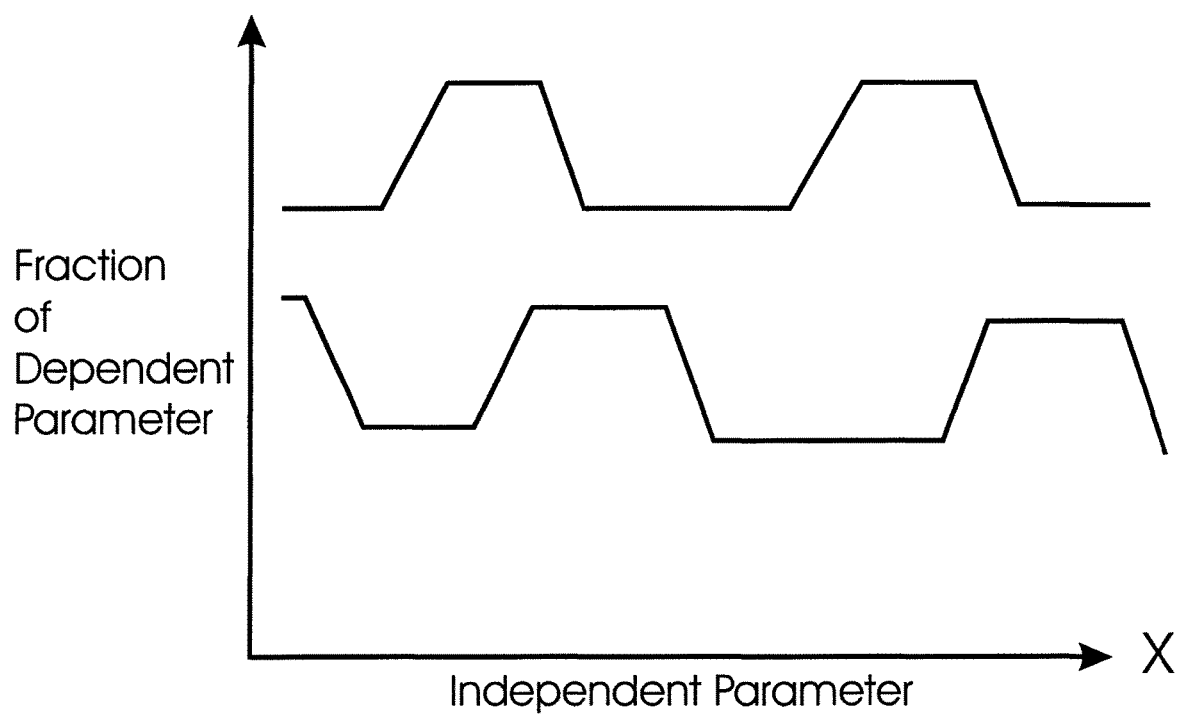
FIG. 20A shows the effect of relative motion on a weight function of the present invention.
Figure 20B:
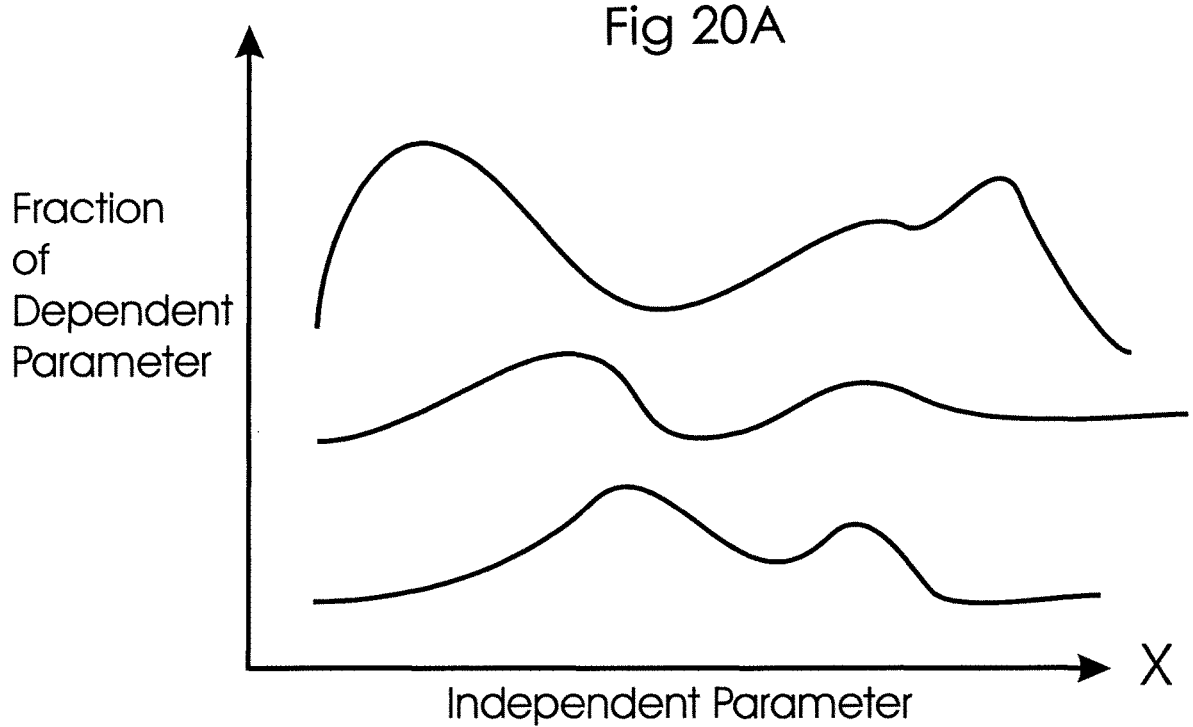
FIG. 20B shows an example of the most general weight function of the present invention.

FIG. 20 shows schematically the general case in which the weight functions are not constant over each region. FIG. 20A shows the general shape of weight functions for a spatial modulator moving relative to the independent parameter at constant velocity during each measurement. As discussed previously, the effect of relative motion can be accounted for by replacing the static weight function values for each range with the time weighted average intensity of particle flux received by the detector from that range during each measurement cycle. FIG. 20B shows the general case in which the weight functions take on values intermediate between 0 and 1 over the entire range of independent parameter x. The measurement protocol of the present invention results in a system of integral equations that can be solved by iterative methods. Approximate solutions can also be obtained by dividing the measurement region into small ranges within which the weight function is nearly constant and the method of Equation 3 is applicable.

The term detector herein refers to any device that produces a response related to incident particle flux integrated over the finite measurement period. A detector can be an integrating device and a detector can be a transducer linked with an integrating device. The term logical detector can refer to a single physical detector or to a plurality of physical detectors measuring particle flux directed along the same path by a modulator.

The invention claimed is:

1. A method for measuring one or more variables of an incident radiation within intervals of an independent variable, where said one or more variables vary dependent on the independent variable, the method comprising the steps of:
collecting the incident radiation to be measured;
directing more than half of incident radiation in each interval into one of at least two distinct paths with a spatial modulator or a temporal modulator, said modulator undergoing a sequence of configurations such that each member of the sequence directs a different combination of incident radiation within intervals into each path;
wherein the sum of radiation intensity for all distinct paths is at least 60% of the total incident radiation;
measuring the total intensity of radiation in each path with a detector for each modulator configuration to provide a plurality of detector outputs;
analyzing the detector outputs statistically to obtain information relating to the dependent variables of the radiation to be measured.

2. The method according to claim 1 wherein said modulator cycles through a sequence of M configurations, in each configuration dividing incident radiation into N portions according to a position and a time that the radiation is incident on the modulator, and directing a majority of each portion of incident radiation into one of P distinct paths; wherein P is greater than or equal to two and less than N and wherein M is greater than or equal to N and the modulator configuration sequence includes at least two configurations for which a majority of each portion is directed into different paths.

3. The method according to claim 1 wherein the radiation is spatially separated by source location, wavelength, phase or polarization and directed into N>2 different regions to be characterized into a measurement surface and wherein the modulator is a spatial modulator placed at said measurement surface.

4. The method according to claim 1 wherein the radiation is temporally divided into N>2 portions using a gate modulator which is modulated according to said sequence.

5. The method according to claim 1 wherein the sequence of configurations of the modulator are chosen such that a matrix representation of the sequence of configurations Z has the property that $Z^TZ$ is non-singular; wherein Z has MP rows and N columns, and wherein each row of Z represents the measurement at one detector and each column of Z represents one range of independent parameter and the elements of Z represent the fraction of particle flux from each range for said row.

6. The method according to claim 1 wherein the radiation is spatially separated by an independent property chosen from the set of source location, wavelength, phase or polarization and directed into N>2 different regions to be characterized into a measurement surface and wherein the modulator is a spatial modulator placed at said measurement surface.

7. The method according to claim 1 wherein the radiation is spatially separated by an independent property where the independent property is time and radiation is temporally separated using a gate modulator.

8. The method according to claim 6 wherein the number of different configurations of the modulator is greater than or equal to the number of divisions of the independent property.

9. The method according to claim 1 wherein the modulator configuration sequence includes at least two configurations for each division in which a majority of radiation within that division is directed into different paths.

10. The method according to claim 1 wherein each path has a plurality of detectors and wherein each detector measures radiation travelling along the path within a different energy range.

11. The method according to claim 1 wherein each path has a plurality of detectors and each detector on a path measures radiation from a different region of origin.

12. The method according to claim 1 wherein the radiation to be measured is from one of the following: a dispersive spectrometer; a Fourier Transform spectrometer; an imaging spectrometer; an interference pattern; a diffractometer; from Raman scattering; a grain kernel, time of flight mass spectrometer, florescent decay, a flow cell for measuring fluid flow, light reflected from particles under analysis, an interference pattern generated by radiation reflected from a vibrating energized solid material and radiation reflected from a reference surface.

13. The method according to claim 1 wherein the spatial modulator is one of: refractive, reflective, diffractive.

14. The method according to claim 1 wherein the detector on each path produces an analog voltage and that analog voltage has a base voltage level subtracted prior to conversion to digital form.

15. The method according to claim 1 wherein the modulator produces cyclic permutations of a base mask with at least two distinct regions.

16. The method according to claim 15 wherein the modulator causes each region of the base mask to direct substantially all of the radiation incident upon that region into a distinct direction.

17. The method according to claim 15 wherein the fraction of the radiation directed into each distinct direction for each measurement region is calculated as the time weighed geometric fraction that the mask region is directing radiation into that direction.

18. The method according to claim 15 wherein the modulator produces a cyclic permutation of the base mask and at least a portion of the mask characteristics are determined by motion of the mask during a measurement period.

19. The method according to claim 1 [20] wherein at least one element of the modulator has at least two different configurations.

20. The method according to claim 15 wherein the modulator comprises dynamic Toeplitz masks and the resolution is varied by changing the sampling rate.

21. The method according to claim 1 wherein each detector output is normalized to the sum of the detector outputs.

22. The method according to claim 1 wherein the properties of the radiation to be measured are obtained by multivariate least squares analysis.

23. The method according to claim 1 wherein the information in the radiation to be measured is obtained by multivariate statistical analysis of the raw detector outputs or the normalized detector outputs.

24. The method according to claim 1 wherein the information in the radiation to be measured is obtained by correlation analysis of the raw detector outputs or the normalized detector outputs.

25. The method according to claim 1 wherein the radiation pattern with N regions is analyzed by statistical analysis to find a smaller number m of latent variables in a spectrum; making m measurements, and using statistical analysis to infer the value of each latent variable.

26. The method according to claim 1 wherein the total intensity of the radiation summed over all detectors varies for at least some of the spatial modulator configurations; and at each modulator configuration, a raw intensity value is generated at each detector; wherein the total intensity for the modulator configuration is C=SUM (detector intensities di) where the data vector is loaded with the values di'=di/C so that this normalization compensates for changes in the intensity.

27. The method according to claim 1 wherein a bandpass filter limits the range of wavelengths propagating through the measurement system to establish boundary conditions for the analysis system.

28. The method according to claim 27 the bandpass filter is further used to optimize the instrument sensitivity for detection measurement in the measurement system of a particular analyte by weighting the transmission of different spectral bands in proportion to the significance of that spectral band to the measurement of the particular analyte.

29. The method according to claim 1 wherein an intensity of the radiation varies for each of a plurality of samples, at each time sample, a raw intensity value is generated at a first detector A and at a second detector B, wherein the total intensity in the time step is C=A+B where the data vector is loaded with the values a'=A/C and b'=B/C so that this normalization compensates for changes in the intensity.

30. The method according to claim 1 including dividing the incident radiation into N packets, each packet containing radiation with a different value of a first property; separating said radiation packets temporally or spatially using a temporal or spatial modulator and varying the modulator using a modulation sequence to direct at least N different combinations of incident radiation packets into at least two distinct paths; including the steps of estimating the time weighted contribution of each band to the total intensity received by each detector in each measurement and setting the coefficients of the Z matrix to explicitly model the time weighted contributions.

31. The method according to claim 1 wherein the spatial modulator and associated optics and detectors are in relative motion with respect to the source of radiation to be measured and the relative motion produces the desired modulation.

32. The method according to claim 1 wherein said modulator cycles through a sequence of M configurations, in each configuration dividing incident radiation into N portions according to a position the radiation is incident on the modulator, and directing a majority of each portion of incident radiation into one of P distinct paths; wherein P is greater than or equal to two and less than N and wherein M is greater than or equal to N and the modulator configuration sequence includes at least two configurations for which a majority of each portion is directed into different paths.

33. The method according to claim 1 wherein said modulator cycles through a sequence of M configurations, in each configuration dividing incident radiation into N portions according to a time the radiation is incident on the modulator, and directing a majority of each portion of incident radiation into one of P distinct paths; wherein P is greater than or equal to two and less than N and wherein M is greater than or equal to N and the modulator configuration sequence includes at least two configurations for which a majority of each portion is directed into different paths.

* * * * *